US011891447B2

(12) United States Patent
Chen et al.

(10) Patent No.: US 11,891,447 B2
(45) Date of Patent: Feb. 6, 2024

(54) METHOD FOR TREATING CANCER USING CD14 ANTAGONISTS

(71) Applicant: Huei-Wen Chen, Taipei (TW)

(72) Inventors: Huei-Wen Chen, Taipei (TW); Pan-Chyr Yang, Taipei (TW); Wan-Jiun Chen, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 124 days.

(21) Appl. No.: 16/637,093

(22) PCT Filed: Aug. 9, 2018

(86) PCT No.: PCT/CN2018/099617
§ 371 (c)(1),
(2) Date: Feb. 6, 2020

(87) PCT Pub. No.: WO2019/029617
PCT Pub. Date: Feb. 14, 2019

(65) Prior Publication Data
US 2020/0181279 A1 Jun. 11, 2020

Related U.S. Application Data

(60) Provisional application No. 62/543,067, filed on Aug. 9, 2017.

(51) Int. Cl.
*A61K 39/00* (2006.01)
*C07K 16/00* (2006.01)
*C07K 16/28* (2006.01)
*A61P 35/00* (2006.01)
*A61K 38/00* (2006.01)

(52) U.S. Cl.
CPC .......... *C07K 16/2896* (2013.01); *A61P 35/00* (2018.01); *A61K 38/00* (2013.01); *A61K 39/00* (2013.01); *A61K 2039/505* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| 6,245,897 B1* | 6/2001 | Adachi | C07K 16/2896 435/332 |
| 7,326,569 B2* | 2/2008 | Leturcq | A61P 29/00 435/326 |
| 8,088,591 B2* | 1/2012 | Franzmann | G01N 33/57407 435/7.23 |
| 9,334,331 B2* | 5/2016 | Igawa | C07K 16/36 |
| 10,421,807 B2* | 9/2019 | Gonzales | A61P 17/08 |
| 2005/0255042 A1* | 11/2005 | Lam | A61K 51/1093 424/1.49 |
| 2007/0134243 A1* | 6/2007 | Gazzard | C07D 221/14 424/145.1 |
| 2010/0331239 A1* | 12/2010 | Tartakovsky | A61P 9/00 514/2.3 |

OTHER PUBLICATIONS

Al Qaraghuli et al. Antibody-protein binding and conformational changes: identifying allosteric signaling pathways to engineer a better effector response. Nature Scientific Reports 10:13969; (2020). (Year: 2020).*
Edwards et al. The remarkable flexibility of the human antibody repertoire; isolation of over one thousand different antibodies to a single protein, BLyS. Journal of Molecular Biology 334:103-118; (2003). (Year: 2003).*
Lloyd et al. Modelling the human immune response: performance of a 10(11) human antibody repertoire against a broad panel of therapeutically relevant antigens. Protein Engineering, Eng. Design & Selection 22(3): 159-168; (2009) (Year: 2009).*
Goel et al. Plasticity within the antigen-combining site may manifest as molecular mimicry in the humoral immune response. J. Immunol. 173: 7358-7367; (2004). (Year: 2004).*
Khan et al. Adjustable locks and flexible keys: plasticity of epitope-paratope interactions in germline antibodies. J. Immunol. 192: 5398-5405; (2014). (Year: 2014).*
Poosarla et al. Computational De Novo Design of Antibodies Binding to a Peptide With High Affinity. Biotechn. Bioeng. 114(6): 1331-1342; (2017). (Year: 2017).*
Rabia et al. Understanding and overcoming trade-offs between antibody affinity, specificity, stability and solubility. Biochemical Engineering Journal 137:365-374; (2018). (Year: 2018).*
Justice et al. (Using the mouse to model human disease: increasing validity and reproducibility, Disease, Models & Mechanisms 9: 101-103, 2016). (Year: 2016).*
Wakabayashi et al. Prevention of metastasis by a polyamine synthesis inhibitor in an animal bone metastasis model. Oncology, 59: 75-80, 2000). (Year: 2000).*
Tokuriki et al. Stability effects of mutations and protein evolvability, Current Opinion in Structural Biology, 19:596-604, (2009). (Year: 2009).*
(Bhattacharya et al. Impact of genetic variation on three dimensional structure and function of proteins; PLOS One 12(3): e0171355 , pp. 1-22, (Mar. 2017). (Year: 2017).*
Clarke et al. Stem Cells and Cancer: Two Faces of Eve. Cell 124:1111-1115 (2006). (Year: 2006).*
Li et al. Overexpression o f CD44 is associated with the occurrence and migration of non-small cell lung cancer; Molecular Medicine Reports vol. 14:3159-3167 (2016). (Year: 2016).*
McCarthy et al. Inflammatory phenotype of classical (CD14++ CD16−) monocytes in patients with advanced non-small cell lung cancer. Journal of Clinical Oncology, vol. 31, No. 15, Supp. Suppl. 1. Abstract No. 11071, ( May 20, 2013). (Year: 2013).*

(Continued)

*Primary Examiner* — Elizabeth C. Kemmerer
*Assistant Examiner* — Regina M DeBerry
(74) *Attorney, Agent, or Firm* — WPAT, P.C.

(57) ABSTRACT

Methods for treating cancer and/or reducing sternness of cancer stem cells in a subject using a CD14 antagonist, which may be an anti-CD14 antibody.

12 Claims, 22 Drawing Sheets

Specification includes a Sequence Listing.

(56) References Cited

OTHER PUBLICATIONS

Huang et al. PD-L1 is a potential negative prognostic factor for non-small cell lung cancer: A 5-year-follow-up study. European Respiratory Journal, Abstract. vol. 38, Supp. Suppl. 55, (Sep. 1, 2011). (Year: 2011).*

InvivoGen Technical Support Page. Anti-hCD14-IgA Neutralizing IgA monoclonal antibody to human CD14. Catalog # maba-hcd14. [online][retrieved on Feb. 210, 2023]. Retrieved from: (www.invivogen.com/sites/default/files/invivogen/products/files/hcd14_iga2tds.pdf). (Year: 1994).*

Ming T. Cheah et al., "CD14-expressing cancer cells establish the inflammatory and proliferative tumor microenvironment in bladder cancer", Proc Natl Acad Sci USA, vol. 112. No. 15, Apr. 14, 2015, pp. 4725-4730.

\* cited by examiner

METHOD FOR TREATING CANCER USING CD14 ANTAGONISTS

CROSS-REFERENCE TO RELATED APPLICATION

This application claims a priority to U.S. Patent Application No. 62/543,067 filed on Aug. 9, 2017, the content of which is incorporated herein in its entirety by reference.

BACKGROUND OF THE INVENTION

1. Field of the Invention

The present invention relates to a method for treating cancer. Particularly, the present invention relates to a method for treating cancer by using CD14 antagonists.

2. The Prior Art

Lung cancer is the most common fatal malignancy worldwide and non-small cell lung cancer (NSCLC) is the most common type of cancer. NSCLC is typically treated using chemotherapy; however, this approach is relatively ineffective providing patients with a median survival of less than one year.

Solid tumors comprise a heterogeneous cell population including a small population of cancer stem cells (CSCs). These cells are believed to cause most malignant tumors and play major roles in cancer recurrence, metastasis and drug resistance. Accordingly, specific agents targeting CSCs may benefit cancer treatment.

SUMMARY OF THE INVENTION

The present disclosure is based on the unexpected discoveries that CD14 is involved in maintaining stemness of cancer stem cells (CSCs) and CD14 antagonists such as anti-CD14 antibodies successfully inhibited sphere forming ability of lung CSCs, and inhibited xenograft tumor formation and tumor growth in mice.

Accordingly, one aspect of the present disclosure provides a method for treating cancer in a subject, comprising administering to a subject in need thereof an effective amount of a CD14 antagonist. In some examples, the amount of the CD14 antagonist is effective in reducing tumor formation or tumor growth in the subject. Alternatively or in addition, the amount of the CD14 antagonist is effective in reducing stemness of cancer stem cells. Alternatively or in addition, the amount of the CD14 antagonist is effective in inhibiting cancer stem cell-induced immunosuppression, e.g., an increased expression of the immunosuppressive ligand PDL1 in immune cells, cancer cells, or both types of cells. Any of the CD14 antagonists may be administered systemically, e.g., via an enteral route or via a parenteral route.

In some embodiments, the CD14 antagonist is an antibody. Any of the antibodies used in the method described herein can be a full-length antibody or an antigen-binding fragment thereof. Alternatively, the antibody can be a human antibody, a humanized antibody, a chimeric antibody, or a single-chain antibody.

Alternatively, the CD14 antagonist is an agent that inhibits a signaling pathway mediated by CD14. In some embodiments, the agent is a small molecule inhibitor or a peptide inhibitor. The CD14 antagonist can also be an agent that inhibits expression of CD14, such as an interfering RNA that targets CD14.

The subject to be treated in the method described herein can be a patient (e.g., a human patient) who has or is suspected of having cancer, for example, lung cancer, breast cancer, colorectal cancer, pancreatic cancer, liver cancer, prostate cancer, skin cancer, lymphoma, or leukemia. In some examples, the subject is a human patient who has or is suspected of having non-small-cell-lung-cancer (NSCLC). Such a human patient may exhibit an elevated level of CD14, PDL1, CD44, or a combination thereof relative to a control subject who does not have cancer (e.g., NSCLC).

Any of the subject to be treated by the method described herein may have been subject to another cancer therapy (e.g., chemotherapy, immune therapy, or surgery). In some embodiments, the method described herein may further comprise administering to the subject another anti-cancer therapeutic agent.

Also within the scope of this disclosure are (a) pharmaceutical compositions for use treating cancer in a subject, the pharmaceutical composition comprising one or more of the CD14 antagonists described herein (e.g., an anti-CD14 antibody) and a pharmaceutically acceptable carrier; and (b) uses of the just-described CD14 antagonist in manufacturing a medicament for cancer treatment.

The details of one or more embodiments of the invention are set forth in the description below. Other features or advantages of the present invention will be apparent from the accompanying drawings and detailed description of several embodiments, and also from the appended claims.

BRIEF DESCRIPTION OF THE DRAWINGS

The accompanying drawings form part of the present specification and are included to further demonstrate certain aspects of the present disclosure, which can be better understood by reference to one or more of these drawings in combination with the detailed description of specific embodiments presented herein.

DETAILED DESCRIPTION OF THE PREFERRED EMBODIMENT

Figure 1A:
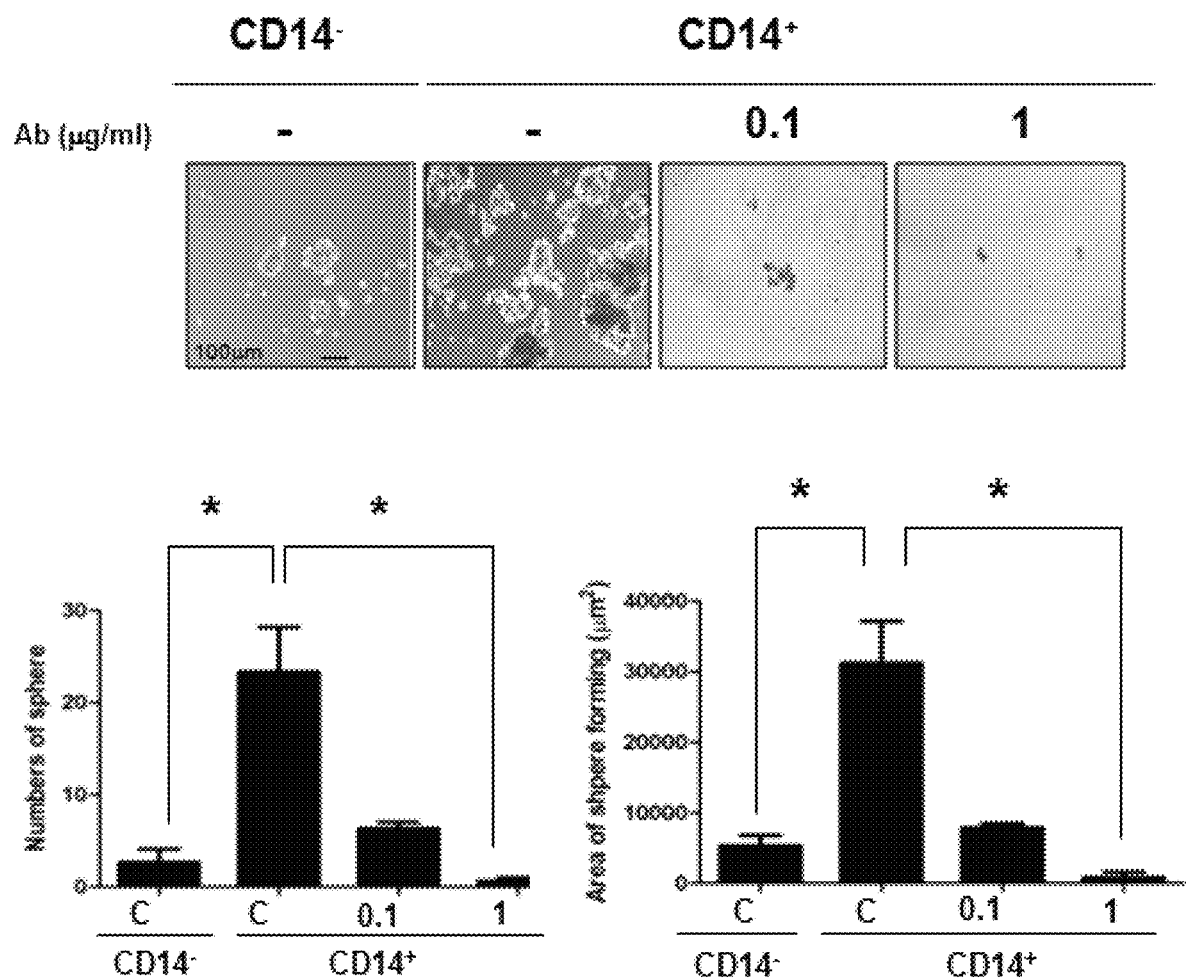
FIGS. 1A-1C show the inhibitory effects of anti-CD14 antibody on the sphere forming capacity of CD14$^+$ lung CSCs. CLS1 (FIG. 1A), CL141 (FIG. 1B) and CL152 (FIG. 1C) cells were cultured in MCDB201 medium with EGF (20 ng/ml) and bFGF (20 ng/ml) in the absence or presence of anti-CD14 antibody (0.1 and 1 µg/ml). After 21 days, morphology (upper panel) and sphere forming ability (lower panel) were determined. Scale bar, 100 µm.

Cancer stem cells (CSCs) are a promising target for treating cancer. CSCs are capable of self-renewal, differentiating into specialized cell types, and developing into cancer. The phenotype of "cancer stemness" may be the driving force behind carcinogenesis, and CSCs are suggested to contribute to chemo- or radio-resistance and metastasis. Increasing evidence shows that CSCs are present in leukemia and in various solid tumors, including lung cancer, breast cancer, colorectal cancer, pancreatic cancer, liver cancer, prostate cancer, skin cancer, lymphoma, or leukemia. CSCs may be identified by biomarkers such as CD14.

The present disclosure reports the unexpected discoveries that (i) CD14 antagonists such as an antiCD14 antibody reduced stemness of cultured CSCs; (ii) the anti-CD14 antibody protected mice from tumor formation and tumor growth; and (iii) CD14-mediated signaling pathway plays an important role in maintaining stemness of cancer stem cells. Accordingly, the present disclosure provides methods of treating a cancer (e.g., alleviating cancer, delaying the onset of cancer, and/or suppressing cancer metastasis) in a subject using an effective amount of a CD14 antagonist, which can be an anti-CD14 antibody or an agent that inhibits a signaling pathway mediated by CD14.

CD14 Antagonists and Pharmaceutical Compositions Comprising Such

CD14 glycoprotein is a co-receptor for bacterial lipopolysaccharide (LPS) and binds LPS in the presence of lipopolysaccharide-binding protein (LBP). There are two isoforms of CD14, a membrane-bound form (mCD14) and a soluble form (sCD14). The term "CD14" used herein encompasses both mCD14 and sCD14 of a subject that expresses CD14, for example, human CD14. As examples, the amino acid sequences of human mCD14 and sCD14 are provided in GenBank accession numbers NP_001167576 and PDB: 4GLP_A.

The CD14 antagonist to be used in the methods described herein can be a molecule that blocks, suppresses, or reduces the signaling pathway mediated by CD14, either directly or indirectly. The term "antagonist" implies no specific mechanism of biological action whatsoever, and is deemed to expressly include and encompass all possible pharmacological, physiological, and biochemical interactions with CD14 whether direct or indirect. For purpose of the present disclosure, it will be explicitly understood that the term "antagonist" encompass all the previously identified terms, titles, and functional states and characteristics whereby the CD14 itself (e.g., human CD14), a CD14 biological activity (including but not limited to its ability to mediate any aspect of cancer), or the consequences of the biological activity, are substantially nullified, decreased, or neutralized in any meaningful degree, e.g., by at least 20%, 50%, 70%, 85%, 90%, 100%, 150%, 200%, 300%, or 500%, or by 10-fold, 20-fold, 50-fold, 100-fold, 1000-fold, or $10^4$-fold.

In some instances, a CD14 antagonist described herein may be an agent that binds to CD14 and inhibits the bioactivity of CD14 directly. In other instances, a CD14 antagonist may be an agent that binds to CD14 and interferes with the interaction between CD14 and its ligand (e.g., LPS), thereby blocking activation of CD14 by the ligand. Alternatively, a CD14 antagonist may be a conjugate comprising a CD14-binding moiety and a toxin moiety. Such a CD14 antagonist may cause toxicity of CD14-expressing cells such as CSCs. In other examples, a CD14 antagonist may be an agent that reduces or suppresses CD14 expression. In addition, a CD14 antagonist may be an agent that acts on a downstream component of the signaling pathway triggered by CD14.

Exemplary CD14 antagonists include, but are not limited to, anti-CD14 antibodies, anti-sense nucleic acid molecules targeting CD14, a small interfering RNA (siRNA) directed toward CD14, CD14 inhibitory small molecule compounds, or CD14 inhibitory peptides.

Anti-CD14 Antibodies

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')$_2$, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An anti-CD14 antibody is an antibody capable of binding to CD14, which may inhibit CD14 biological activity and/or downstream pathway(s) mediated by CD14 signaling. In some examples, an anti-CD14 antibody used in the methods described herein suppresses the CD14 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. Examples of anti-CD14 antibodies include, but are not limited to, those disclosed in U.S. Pat. Nos. 6,245,897; and 7,326,569; and PCT publications WO 2002/042333; and WO 2015/140591. In some instances, the anti-CD14 antibody binds the extracellular domain of CD14 or an epitope therein.

The binding affinity of an anti-CD14 antibody to CD14 (such as human CD14) can be less than any of about 100 nM, about 50 nM, about 10 nM, about 1 nM, about 500 pM, about 100 pM, or about 50 pM to any of about 2 pM. Binding affinity can be expressed $K_D$ or dissociation constant, and an increased binding affinity corresponds to a decreased $K_D$. One way of determining binding affinity of antibodies to CD14 is by measuring binding affinity of monofunctional Fab fragments of the antibody. To obtain monofunctional Fab fragments, an antibody (for example, IgG) can be cleaved with papain or expressed recombinantly. The affinity of an anti-CD14 Fab fragment of an antibody can be determined by surface plasmon resonance (BIAcore3000™ surface plasmon resonance (SPR) system, BIAcore, INC, Piscaway N.J.). Kinetic association rates ($k_{on}$) and dissociation rates ($k_{off}$) (generally measured at 25° C.) are obtained; and equilibrium dissociation constant ($K_D$) values are calculated as $k_{off}/k_{on}$.

In some embodiments, the antibody binds human CD14, and does not significantly bind a CD14 from another mammalian species. In some embodiments, the antibody binds human CD14 as well as one or more CD14 from another mammalian species. In still other embodiments, the antibody binds CD14 and does not significantly cross-react with other proteins. The epitope(s) bound by the antibody can be continuous or discontinuous.

The anti-CD14 antibodies to be used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogenous antibody population. These two terms do not limit the source of an antibody or the manner in which it is made.

In some embodiments, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In some embodiments, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In some examples, the antibody disclosed herein specifically binds a target antigen, such as human CD14 (e.g., human mCD14 or human sCD14). An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to a CD14 epitope is an antibody that binds this CD14 epitope with greater affinity, avidity, more readily, and/or with greater duration than it binds to other CD14 epitopes or non-CD14 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

Antibodies capable of interfering with the CD14 signaling pathway can be an antibody that binds a CD14 (e.g., a human CD14) and inhibits CD14 biological activity and/or downstream pathways mediated by CD14. Alternatively, such antibodies can be antibodies that bind a CD14 ligand (e.g., LBP), bind to one or more of the Toll-Like Receptors (TLRs), and suppress the downstream signaling pathways mediated by CD14.

Any of the anti-CD14 antibodies described herein may be conjugated to a toxin to form an antibody-drug conjugate. In some examples, the anti-CD14 antibody may bind a CD14 (e.g., a human CD14) with minimal effect on the CD14 signaling pathway. Examples of toxins include, but are not limited to, abrin, ricin A, *pseudomonas* exotoxin, or diphtheria toxin. In some embodiments, the toxin is a cytotoxic agent such as taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Antibodies capable of interfering with the CD14 signaling pathway (e.g., anti-CD14 antibodies) as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., human CD14) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-CD14 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the CD14 signaling pathway. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or $R_1N=C=NR$, where R and $R_1$ are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the signaling pathway mediated by CD14. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as *E. coli* cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., *Proc. Natl. Acad. Sci. USA,* 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to CD14 can be identified from the library following routine procedures. Positive clones can be subjected to further screening to identify those that suppress CD14 receptor activity.

Antibodies obtained following a method known in the art and described herein can be characterized using methods well known in the art. For example, one method is to identify the epitope to which the antigen binds, or "epitope mapping". There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the CD14 polypeptide have been replaced (swapped) with sequences from a closely related, but antigenically distinct protein. By assessing binding of the antibody to the mutant CD14, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Other CD14 Antagonists

CD14 antagonists other than antibodies described above can be used in the methods described herein. In some embodiments, the CD14 antagonist is an agent that inhibits a signaling pathway mediated by CD14, for example, a small molecule inhibitor or a peptide inhibitor that directly inhibits the activity of CD14, or an agent that inhibits expression of CD14 (e.g., an interfering RNA that targets CD14).

In other embodiments, the CD14 antagonist comprises at least one CD14 inhibitory compound. As used herein, "CD14 inhibitory compound" refers to a compound other than an anti-CD14 antibody that directly or indirectly reduces, inhibits, neutralizes, or abolishes CD14 biological activity. An CD14 inhibitory compound should exhibit any one or more of the following characteristics: (a) binds to CD14 and inhibits its biological activity and/or downstream pathways mediated by CD14 signaling function; (b) prevents, ameliorates, or treats any aspect of a cancer; (c) reduces stemness of CSCs; (d) reduces tumor formation or tumor growth; (e) blocks or decreases CD14 receptor activation; (f) increases clearance of CD14; (g) inhibits (reduces) CD14 synthesis, production or release. One skilled in the art can prepare other small molecules inhibitory compounds.

In some embodiments, an CD14 inhibitory compound can be a CD14 mutant, a Toll-like receptor TLR 4 mutant, an MD-2 mutant, a lipopolysaccharide-binding protein (LBP) mutant, or a lipopolysaccharide (LPS) mutant, which can bind to CD14 but cannot elicit signal transduction. Such a mutant may block binding of wild type LPS to CD14 thus preventing CD14 signal transduction.

In other embodiments, the CD14 inhibitory compounds described herein are small molecules, which can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the CD14 antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al. J. Med. Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

In some embodiments, the small molecule inhibitor may be a glycolipid or a benzylammonium lipid. Examples of commercially available small molecule inhibitors include, but are not limited to, IAXO-101, IAXO-102, and IAXO-3.

In other embodiments, the CD14 antagonists can be a polypeptide comprising a portion of a CD14-binding protein, wherein the polypeptide specifically binds to CD14 and blocks its interaction with one or more CD14 binding proteins. Examples of the CD14-binding proteins are LPS, LBP, and TRL4. Alternatively, the CD14 antagonists may be an agent that decreases CD14 expression, for example, morpholino oligonucleotides, small interfering RNA (siRNA or RNAi), antisense nucleic acids, or ribozymes. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene.

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792, 608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3', 5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim Acta, 1995, 78, 486-504.

In yet another example, the nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and O-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

CD14 antagonists can be identified or characterized using methods known in the art, whereby reduction, amelioration, or neutralization of a CD14 biological activity is detected and/or measured. For example, an ELISA-type assay may be suitable for qualitative or quantitative measurement of CD14 binding to lipopolysaccharide-binding protein (LBP) and lipopolysaccharide (LPS).

The CD14 antagonists can also be identified by incubating a candidate agent with CD14 and monitoring any one or more of the following characteristics: (a) binding to CD14 and inhibiting its biological activity and/or downstream pathways mediated by CD14 signaling; (b) preventing, ameliorating, or treating any aspect of a cancer; (c) blocking or decreasing CD14 receptor activation; (d) increasing clearance of CD14; (e) inhibiting (reducing) CD14 synthesis, production or release. In some embodiments, a CD14 antagonist is identified by incubating a candidate agent with CD14 and monitoring binding and attendant reduction or neutralization of a biological activity of CD14. The binding assay may be performed with purified CD14 polypeptide(s), or with cells naturally expressing, or transfected to express, CD14 polypeptide(s). In one embodiment, the binding assay is a competitive binding assay, where the ability of a candidate antibody to compete with a known CD14 antagonist for CD14 binding is evaluated. The assay may be performed in various formats, including the ELISA format. In other embodiments, a CD14 antagonist is identified by incubating a candidate agent with CD14 and monitoring attendant inhibition of CD14/LPS complex formation or CD14/LPS/LBP complex formation. Following initial identification, the activity of a candidate CD14 antagonist can be further confirmed and refined by bioassays, known to test the targeted biological activities. Alternatively, bioassays can be used to screen candidates directly.

The examples provided below provide a number of assays that can be used to screen candidate CD14 antagonists. Bioassays include but are not limited to assaying, in the presence of CD14 antagonists, receptor-associated tyrosine kinase (TK) activity or assaying translocation of nuclear factor-kappa B (NF-κB). In addition, Real-Time PCR (RT-PCR) can be used to directly measure CD14 expression or to measure expression of genes upregulated by CD14 such as CD44 and PDL1.

Further, a suitable CD14 antagonist may be screened from a combinatory compound library using any of the assay methods known in the art and/or described herein.

Pharmaceutical Compositions

One or more of the above-described CD14 antagonist can be mixed with a pharmaceutically acceptable carrier (excipient), including buffer, to form a pharmaceutical composition for use in alleviating cancer. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover. In one example, a pharmaceutical composition described herein contains more than one anti-CD14 antibodies that recognize different epitopes of the target antigen. In another example, the pharmaceutical composition comprises at least two different-typed CD14 antagonists (e.g., one antibody and one small molecule).

The pharmaceutical compositions to be used in the present methods can comprise pharmaceutically acceptable carriers, excipients, or stabilizers in the form of lyophilized formulations or aqueous solutions (Remington: The Science and Practice of Pharmacy $20^{th}$ Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ (polysorbate), PLURONICS™ (poloxamers) or polyethylene glycol (PEG). Pharmaceutically acceptable excipients are further described herein.

In some examples, the pharmaceutical composition described herein comprises liposomes containing the CD14 antagonist (such as an antibody), which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients (e.g., an CD14 antagonist) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are known in the art, see, e.g., Remington, The Science and Practice of Pharmacy 20$^{th}$ Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a CD14 antagonist with Intralipid™ (a lipid emulsion) or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Use of CD14 Antagonists for Treating Cancer

To practice the method disclosed herein, an effective amount of the pharmaceutical composition described above can be administered to a subject (e.g., a human) in need of the treatment via a suitable route (e.g., intravenous administration).

The subject to be treated by the methods described herein can be a human patient having, suspected of having, or at risk for a cancer. Examples of a cancer include, but are not limited to, lung cancer, non-small-cell-lung-cancer (NSCLC), breast cancer, colorectal cancer, pancreatic cancer, liver cancer, prostate cancer, skin cancer, lymphoma, or leukemia. The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a cancer (e.g., lung cancer). A subject having a cancer can be identified by routine medical examination, e.g., laboratory tests, biopsy, PET scans, CT scans, or ultrasounds. A subject suspected of having a cancer might show one or more symptoms of the disorder, e.g., unexplained weight loss, fever, fatigue, cough, pain, skin changes, unusual bleeding or discharge, and/or thickening or lumps in parts of the body. A subject at risk for a cancer can be a subject having one or more of the risk factors for that disorder. For example, risk factors associated with cancer include (a) viral infection (e.g., herpes virus infection), (b) age, (c) family history, (d) heavy alcohol consumption, (e) obesity, and (f) tobacco use.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of a cancer. Alternatively, sustained continuous release formulations of a CD14 antagonist may be appropriate. Various formulations and devices for achieving sustained release are known in the art.

In one example, dosages for a CD14 antagonist as described herein may be determined empirically in individuals who have been given one or more administration(s) of CD14 antagonist. Individuals are given incremental dosages of the antagonist. To assess efficacy of the antagonist, an indicator of a cancer (such as tumor formation or tumor growth) can be followed.

Generally, for administration of any of the antibodies described herein, an initial candidate dosage can be about 2 mg/kg. For the purpose of the present disclosure, a typical daily dosage might range from about any of 0.1 μg/kg to 3 μg/kg to 30 μg/kg to 300 μg/kg to 3 mg/kg, to 30 mg/kg to 100 mg/kg or more, depending on the factors mentioned above. For repeated administrations over several days or longer, depending on the condition, the treatment is sustained until a desired suppression of symptoms occurs or until sufficient therapeutic levels are achieved to alleviate a cancer, or a symptom thereof. An exemplary dosing regimen comprises administering an initial dose of about 2 mg/kg, followed by a weekly maintenance dose of about 1 mg/kg of the antibody, or followed by a maintenance dose of about 1 mg/kg every other week. However, other dosage regimens may be useful, depending on the pattern of pharmacokinetic decay that the practitioner wishes to achieve. For example, dosing from one-four times a week is contemplated. In some embodiments, dosing ranging from about 3 μg/mg to about 2 mg/kg (such as about 3 μg/mg, about 10 μg/mg, about 30 μg/mg, about 100 μg/mg, about 300 μg/mg, about 1 mg/kg, and about 2 mg/kg) may be used. In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the antibody used) can vary over time.

When the CD14 antagonist is not an antibody, it may be administered at the rate of about 0.1 to 300 mg/kg of the weight of the patient divided into one to three doses, or as disclosed herein. In some embodiments, for an adult patient of normal weight, doses ranging from about 0.3 to 5.00 mg/kg may be administered. The particular dosage regimen, i.e., dose, timing and repetition, will depend on the particular individual and that individual's medical history, as well as the properties of the individual agents (such as the half-life of the agent, and other considerations well known in the art).

For the purpose of the present disclosure, the appropriate dosage of a CD14 antagonist will depend on the specific CD14 antagonist(s) (or compositions thereof) employed, the type and severity of cancer, whether the antagonist is administered for preventive or therapeutic purposes, previous therapy, the patient's clinical history and response to the antagonist, and the discretion of the attending physician.

Typically the clinician will administer a CD14 antagonist, such as an anti-CD14 antibody, until a dosage is reached that achieves the desired result. Administration of a CD14 antagonist can be continuous or intermittent, depending, for example, upon the recipient's physiological condition, whether the purpose of the administration is therapeutic or prophylactic, and other factors known to skilled practitioners. The administration of a CD14 antagonist (for example if the CD14 antagonist is an anti-CD14 antibody) may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the disorder, the symptom of the disease, or the predisposition toward a cancer.

Alleviating a cancer includes delaying the development or progression of the disease, or reducing disease severity. Alleviating the disease does not necessarily require curative results. As used therein, "delaying" the development of a disease (such as lung cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

In some embodiments, the CD14 antagonist (e.g., an anti-CD14 antibody) described herein is administered to a subject in need of the treatment at an amount sufficient to reduce the level of CD14-mediated signaling by at least 20% (e.g., 30%, 40%, 50%, 60%, 70%, 80%, 90% or greater). In other embodiments, the antagonist is administered in an amount effective in reducing stemness of CSCs. Alternatively, the antagonist is administered in an amount effective in reducing tumor formation or tumor growth.

In some embodiments, the CD14 antagonist is administered to a subject in need of the treatment at an amount sufficient to reducing stemness of cancer stem cells by at least 20% (e.g., 30%, 40%, 50%, 60%, 70%, 80%, 90% or greater). Stemness of cancer cells refers to the ability of cancer stem cells to self-renew and differentiate into different tumor cell types. The level of cancer cell stemness can be determined by a conventional assay or by the assays described herein (see Examples below).

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, a CD14 antagonist is administered via site-specific or targeted local delivery techniques. Examples of site-specific or targeted local delivery techniques include various implantable depot sources of the CD14 antagonist or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 μg to about 2 mg, about 5 μg to about 500 μg, and about 20 μg to about 100 μg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the protein-based CD14 antagonists described herein (e.g., anti-CD14 antibody). For example, other CD14 peptide inhibitors that are capable of blocking (from partial to complete blocking) CD14 and/or a CD14 biological activity are known in the art.

The particular dosage regimen, i.e., dose, timing and repetition, used in the method described herein will depend on the particular subject and that subject's medical history.

In some embodiments, more than one CD14 antagonist, such as an antibody and a small molecule CD14 inhibitory compound, may be administered to a subject in need of the treatment. The antagonist can be the same type or different from each other. At least one, at least two, at least three, at least four, at least five different CD14 antagonists can be co-administered. Generally, those CD14 antagonists have complementary activities that do not adversely affect each other. CD14 antagonists can also be used in conjunction with other agents that serve to enhance and/or complement the effectiveness of the agents.

Treatment efficacy can be assessed by methods well-known in the art, e.g., monitoring tumor growth or formation in a patient subjected to the treatment. See, e.g., Example 1 below.

Combination Therapy

Also provided herein are combined therapies using any of the CD14 antagonists described herein and another anti-cancer therapeutic agent, such as those described herein. The term combination therapy, as used herein, embraces administration of these agents (e.g., a CD14 antagonist and an anti-cancer therapeutic agent) in a sequential manner, that is, wherein each therapeutic agent is administered at a different time, as well as administration of these therapeutic agents, or at least two of the agents, in a substantially simultaneous manner.

Sequential or substantially simultaneous administration of each agent can be affected by any appropriate route including, but not limited to, oral routes, intravenous routes, intramuscular, subcutaneous routes, and direct absorption through mucous membrane tissues. The agents can be administered by the same route or by different routes. For example, a first agent (e.g., a CD14 antagonist) can be administered orally, and a second agent (e.g., an anti-cancer agent) can be administered intravenously.

As used herein, the term "sequential" means, unless otherwise specified, characterized by a regular sequence or order, e.g., if a dosage regimen includes the administration of a CD14 antagonist and an anti-cancer agent, a sequential dosage regimen could include administration of the CD14 antagonist before, simultaneously, substantially simultaneously, or after administration of the anti-cancer agent, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents described herein.

Combination therapy can also embrace the administration of the agents described herein (e.g., a CD14 antagonist and an anti-cancer agent) in further combination with other biologically active ingredients (e.g., a different anti-cancer agent) and non-drug therapies (e.g., surgery).

It should be appreciated that any combination of a CD14 antagonist and another anti-cancer agent (e.g., a chemotherapeutic agent) may be used in any sequence for treating a cancer. The combinations described herein may be selected on the basis of a number of factors, which include but are not limited to the effectiveness of inhibiting CD14, reducing tumor formation or tumor growth, reducing stemness of CSCs, and/or alleviating at least one symptom associated with the cancer, or the effectiveness for mitigating the side effects of another agent of the combination. For example, a combined therapy described herein may reduce any of the side effects associated with each individual members of the combination, for example, a side effect associated with the anti-cancer agent.

In some embodiments, another anti-cancer therapeutic agent is a chemotherapy, a radiation therapy, a surgical therapy and/or an immunotherapy. Examples of the chemotherapeutic agents include, but are not limited to, Carboplatin or Cisplatin, Docetaxel, Gemcitabine, Nab-Paclitaxel, Paclitaxel, Pemetrexed, and Vinorelbine. Examples of radiation therapy include, but are not limited to, ionizing radiation, gamma-radiation, neutron beam radiotherapy, electron beam radiotherapy, proton therapy, brachytherapy, systemic radioactive isotopes and radiosensitizers. Examples of a surgical therapy include, but are not limited to, a curative surgery (e.g., tumor removal surgery), a preventive surgery, a laparoscopic surgery, and a laser surgery. Examples of an immunotherapy include, but are not limited to, a PD-1 inhibitor or a PD-L1 inhibitor, adoptive cell transfer, and therapeutic cancer vaccines.

Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin HCl, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives); Purine antagonists (Thioguanine, Fludarabine, Cladribine, 6-Mercaptopurine, Pentostatin, clofarabine and relatives) and Pyrimidine antagonists (Cytarabine, Floxuridine, Azacitidine, Tegafur, Carmofur, Capacitabine, Gemcitabine, hydroxyurea, 5-Fluorouracil (5FU), and relatives); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives); nitrosoureas (e.g., Carmustine, Lomustine, Semustine, Fotemustine, Nimustine, Ranimustine, Streptozocin, and relatives); Triazenes (e.g., Dacarbazine, Altretamine, Temozolomide, and relatives); Alkyl sulphonates (e.g., Busulfan, Mannosulfan, Treosulfan, and relatives); Procarbazine; Mitobronitol, and Aziridines (e.g., Carboquone, Triaziquone, ThioTEPA, triethylenemalamine, and relatives); Antibiotics, such as Hydroxyurea, Anthracyclines (e.g., doxorubicin agent, daunorubicin, epirubicin and other derivatives); Anthracenediones (e.g., Mitoxantrone and relatives); *Streptomyces* family (e.g., Bleomycin, Mitomycin C, Actinomycin, Plicamycin); and Ultraviolet light.

Kits for Use in Treating Cancer

The present disclosure also provides kits for use in alleviating cancer. Such kits can include one or more containers comprising a CD14 antagonist (e.g., an anti-CD14 antibody). In some embodiments, the CD14 antagonist is any agent capable of interfering with the CD14 signaling pathway as described herein. In other embodiments, the kit comprises a CD14 antagonist that is a small molecule inhibitor, a peptide inhibitor, or an agent that inhibits expression of CD14.

In some embodiments, the kit can comprise instructions for use in accordance with any of the methods described herein. The included instructions can comprise a description of administration of the CD14 antagonist to treat, delay the onset, or alleviate a cancer according to any of the methods described herein. The kit may further comprise a description of selecting an individual suitable for treatment based on identifying whether that individual has cancer. In still other embodiments, the instructions comprise a description of administering a CD14 antagonist to an individual having, suspected of having, or at risk for a cancer.

The instructions relating to the use of a CD14 antagonist generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a CD14 antagonist, such as an anti-CD14 antibody.

Kits may optionally provide additional components such as buffers and interpretive information. Normally, the kit comprises a container and a label or package insert(s) on or associated with the container. In some embodiments, the invention provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

EXAMPLES

Example 1: Protective Effect of Anti-CD14 Antibody Against Human Lung Cancer Stem Cells Materials and Methods
Lung Cancer Cell Lines Human lung cancer cell lines (CLS1, CL141 and CL152) were established using primary cultures from lung cancer patients. The cells were cultured in RPMI 1640 medium supplemented with 10% FBS at 37° C. under a humidified atmosphere consisting of 20% $O_2$ and 5% $CO_2$.
Ultra-Low Sphere Forming Assay An ultra-low sphere-forming assay was performed according to standard procedures and modified as described herein. A single-cell suspension of lung CSCs in MCDB201 serum-free medium (Invitrogen) supplemented with 20 ng/ml EGF (Sigma) and 20 ng/ml bFGF (Invitrogen) was seeded in ultra-low adherent 24-well plates (Corning, Corning, N.Y., USA; 200 viable cells/well). The medium was supplemented with fresh growth factors twice weekly. After 3 weeks, the spheres were examined under the Axiovert 200 microscope.
Xenograft Tumor Formation in SCID Mice All procedures involving mice were approved by the Animal Care and Use Committee of the National Taiwan University. Six-week-old male SCID mice or NOD/SCID/IL2Rγ_(NSG) mice were used for the subcutaneous injection of lung cancer cells or CSCs in low doses ($10^4$, $10^3$ or $10^2$ viable cells in 100 µl of PBS mixed in Matrigel). The mice were monitored for 8 weeks, and the incidence of tumor formation and metastasis was examined. The tumor sections were stained with hematoxylin and eosin (H&E).

Figure 1B:
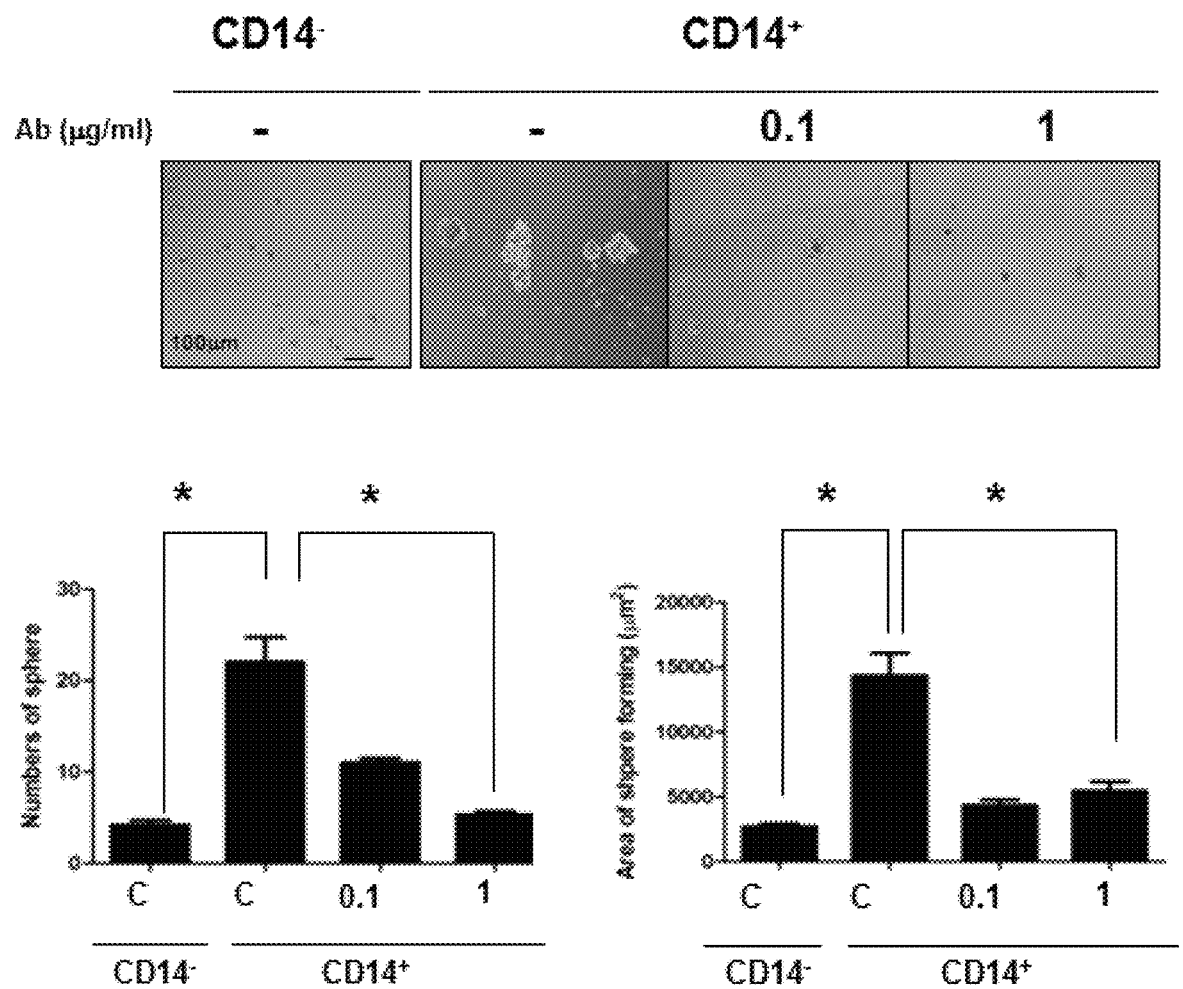
Figure 1C:
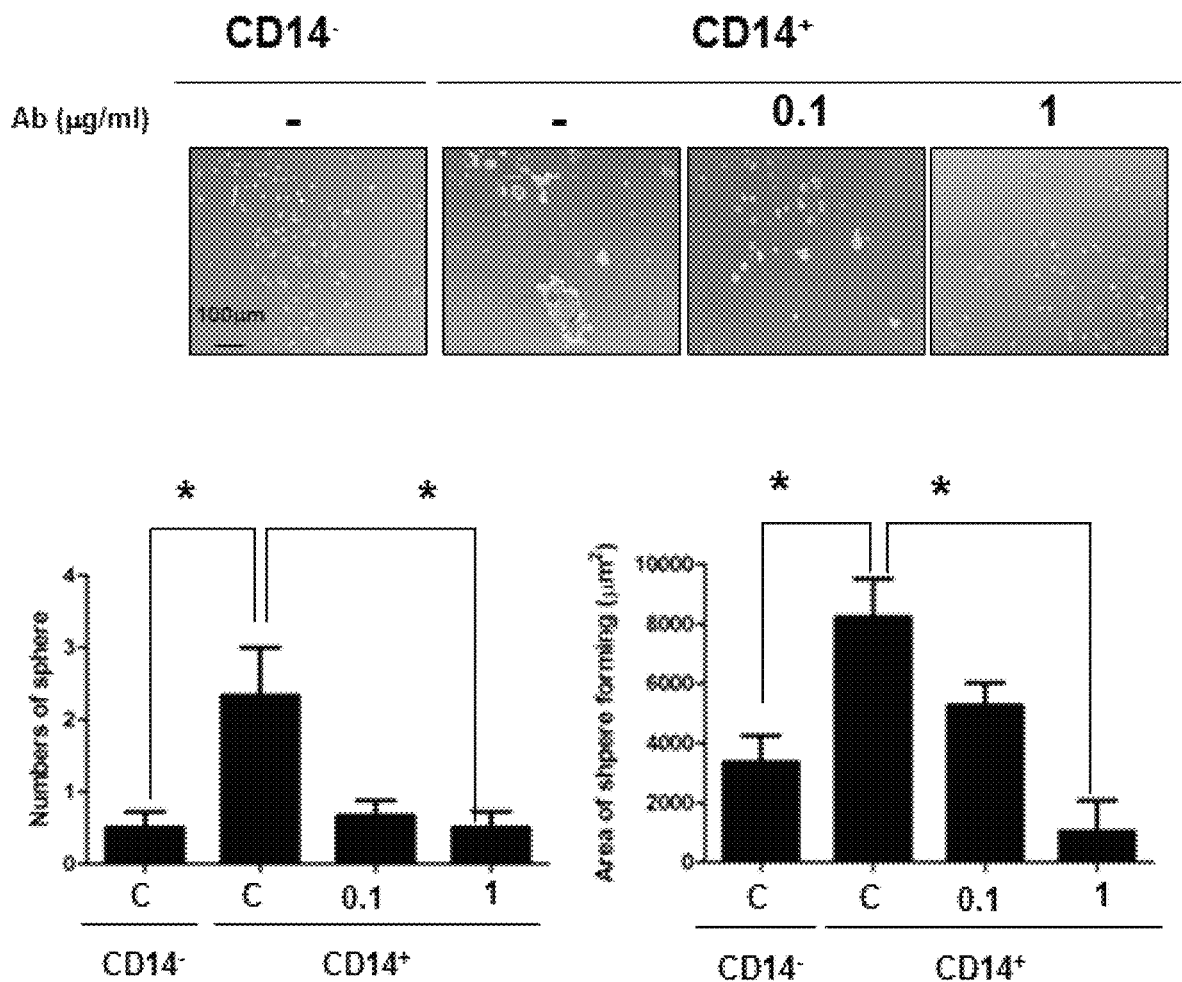
Figure 2A:
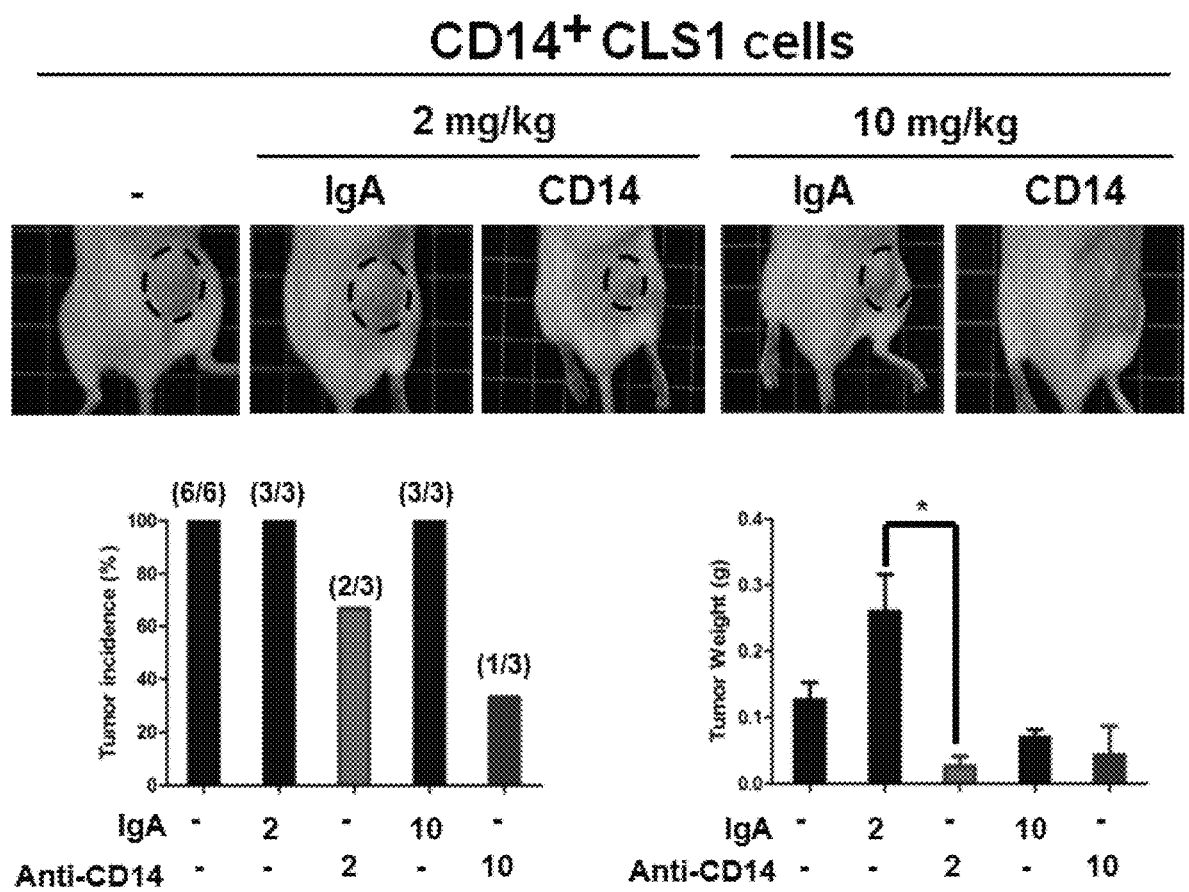
FIGS. 2A-2B show the inhibitory effects of anti-CD14 antibody on tumor initiation (FIG. 2A) and tumor growth in mice (FIG. 2B). The incidence and tumor weight of xenograft tumors formed from CD14$^+$ CLS1 cells was determined following treatment with 2 or 10 mg/kg of anti-CD14 antibody once a week for two weeks. Tumors were generated by injection of 500 CD14$^+$ CLS1 cells (N≥3 mice) (FIG. 2A). The tumor growth of xenograft tumors formed from CD14$^+$ CLS1 cells was determined following treatment with 1, 2 or 5 mg/kg of anti-CD14 antibody twice a week for two weeks. Tumors were generated by injection of 500 CD14$^+$ CLS1 cells (N≥3 mice) (FIG. 2B).

For in vivo experiments, a total of 500 CD14$^+$ cancer cells sorted from CLS1 cells were s.c. injected into mice in a 100-mL volume. For tumor initiating assessment, mice were randomized into 5 groups (anti-CD14 antibody at 2 and 10 mg/kg, IgA antibody at 2 and 10 mg/kg, and vehicle control) and administered anti-CD14 antibody, IgA antibody, or vehicle control once a week for two weeks. Tumor incidence and tumor weight were measured on day 30 and presented as mean±SEM. For tumor growth assessment, mice having an average tumor volume growth of 50 µm$^3$ were randomized into 6 groups (anti-CD14 antibody at 1, 2 and 10 mg/kg and IgA antibody at 1,2 and 10 mg/kg) and administered anti-CD14 antibody or IgA antibody twice a week for two weeks. Tumor volume was monitored twice a week by electronic vernier caliper and calculated using the formula Volume=0.4×ab$^2$, where a and b are the longest and shortest diameters of the tumors, respectively.
Statistical Analysis The quantitative in vitro and in vivo data are presented as the mean±standard error (S.E.M) unless otherwise noted. Student's t-tests were used in two group comparisons. All tests were two-tailed and P values <0.05 were considered significant.
Results
Anti-CD14 Antibody Inhibited Sphere Formation of CD14$^+$ Lung Cancer Cells To determine whether anti-CD14 antibody could inhibit formation of CD14$^+$ lung cancer stem cells, the sphere-forming ability of CLS1, CL141, and CL152 lung cancer cells was determined in the absence and presence of increasing concentrations of anti-CD14 antibody. The sphere forming ability of CLS1 (FIG. 1A), CL141 (FIG. 1B), and CL152 (FIG. 1C) lung cancer cells was inhibited by anti-CD14 antibody in a dose-dependent manner. These results indicate that CD14 is a target for reducing stemness of primary lung cancer stem cells and thus a promising target for cancer treatment.
Anti-CD14 Antibody Protected Mice from Tumor Formation and Tumor Growth To determine whether anti-CD14 antibody could inhibit tumor formation, mice were subcutaneously inoculated with CD14$^+$ CLS1 cells (500 cells) and administered anti-CD14 antibody, IgA antibody, or vehicle control. Mice treated with anti-CD14 antibody had significantly reduced tumor formation and tumor weight compared to mice treated with IgA antibody control or vehicle control (FIG. 2A). These reductions were observed in a dose-dependent manner (FIG. 2A). These results indicate that anti-CD14 antibody treatment protects against tumor formation of CD14$^+$ lung cancer cells.

Figure 2B:
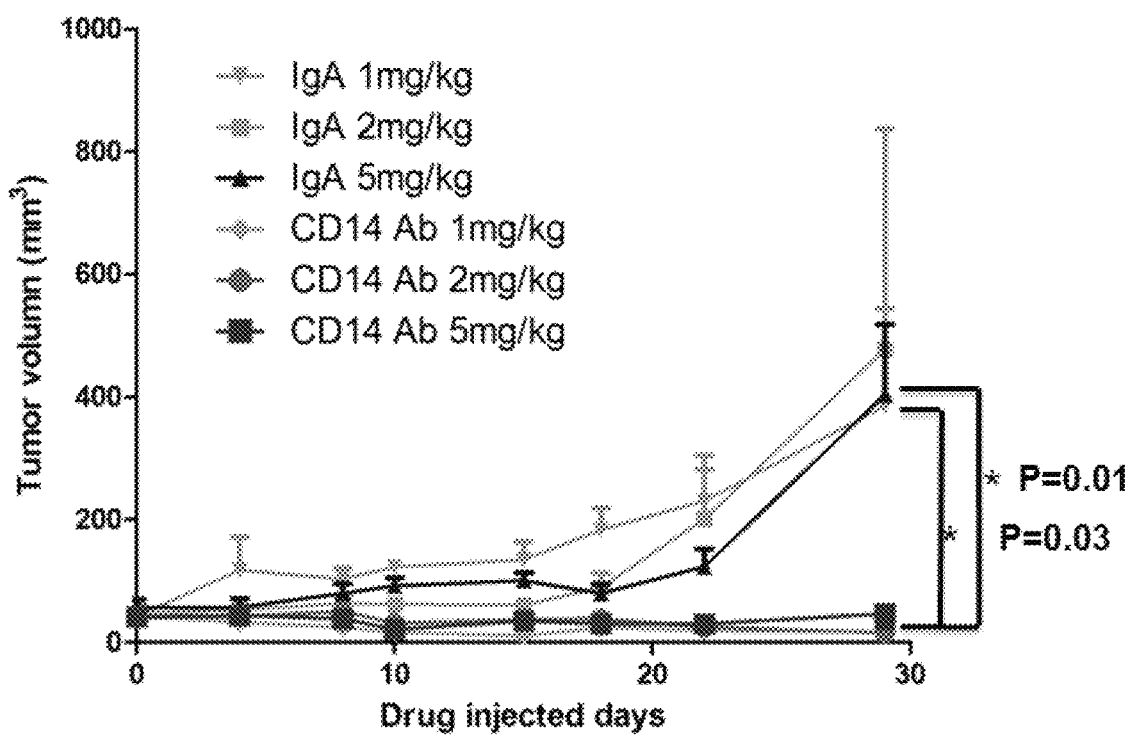

To determine whether anti-CD14 antibody could inhibit tumor growth, mice having generated a tumor after inoculation with CD14$^+$ CLS1 cells were treated with anti-CD14 antibody or IgA antibody. Mice treated with anti-CD14 antibody had a 40% reduction in tumor volume compared to mice treated with IgA antibody control (FIG. 2B). These results indicate that anti-CD14 antibody treatment protects against tumor growth of CD14$^+$ lung cancer cells.

Example 2: Identification of CD14-Specific Signaling Pathways in Lung CSCs

Materials and Methods
Real-Time Reverse Transcriptase (RT) Q-PCR

The expression level of stemness-related genes and validation of the Affymetrix microarray data for CD14 overexpression CLS1 and Mock CLS1 cells were performed through RT Q-PCR using an ABI Prism 7900 Sequencer (Applied Biosystems). The primers were designed using Primer Express 3.0 (Applied Biosystems) (Table 1). β-actin were used as internal controls. The expression levels were normalized to β-actin and defined as $-\Delta CT = -[CT_{target} - CT_{\beta-actin}]$. The relative expression ratio was calculated as the fold change relative to the control ($2^{-\Delta\Delta CT}$). The experiments were performed in triplicate.

TABLE 1

Primers for RT Q-PCR

| Gene Symbol | UniGene ID | Forward primer | Reverse primer |
| --- | --- | --- | --- |
| CD14 | Hs.163867 | CACAGAGGAGGG AACTGAATGAC (SEQ ID NO: 1) | AACTCTTCGGCT GCCTCTGA (SEQ ID NO: 2) |
| CD44 | Hs.502328 | TGGACACTCACA TGGGAGTCAAGA (SEQ ID NO: 3) | CGACTGTTGACT GCAATGCA (SEQ ID NO: 4) |
| ALDH1A1 | NM_000689 | TCCAGCCCACAG TGTTCTCTAAT (SEQ ID NO: 5) | ACTGGTCCAAAA ATCTCCTCTTTG (SEQ ID NO: 6) |

TABLE 1-continued

Primers for RT Q-PCR

| Gene Symbol | UniGene ID | Forward primer | Reverse primer |
|---|---|---|---|
| ABCG1 | NM_004915 | CCAGCTTTACGT CCTGAGTCAA (SEQ ID NO: 7) | GACCCAAATCCC TCAAATATGG (SEQ ID NO: 8) |
| ABCG2 | NM_001257386 | GCTCAGATCATT GTCACAGTCGTA CT (SEQ ID NO: 9) | GTTGGTCGTCAG GAAGAAGAGAA (SEQ ID NO: 10) |
| PDL1 | NM_001267706 | CCTCTGGCACAT CCTCCAAA (SEQ ID NO: 11) | TCACATCCATCA TTCTCCCTTTTC (SEQ ID NO: 12) |
| ACTB | Hs.520640 | CTGGAACGGTGA AGGTGACA (SEQ ID NO: 13) | CGGCCACATTGT GAACTTTG (SEQ ID NO: 14) |

Gene Expression Profiling

The gene expression profiling map of CD14 overexpressed in CLS1 cells and Mock CLS1 cells were obtained using the AffymetrixGeneChip system (Affymetrix, Inc., Santa Clara, Calif., USA) according to the manufacturer's protocol. The array data were processed by the National Taiwan University Microarray Core Facility for Genomic Medicine. Briefly, total RNA isolated from CAFs, lung CSCs and cancer cells was used to generate cDNA (SuperscriptChoice System, Gibco BRL Life Technologies) with T7-(dT)$_{24}$ primers. Biotin-labeled ribonucleotides were synthesized using a BioArray high-yield RNA transcript labeling kit (EnzoDiagnostic, Inc.) and hybridized onto the human Genome U133 Plus 2.0 chip (Affymetrix).

Flow Cytometry

Population of cancer stem cell markers was analyzed and sorted by flow cytometry. Antibodies for the human antigens CD14 PE-conjugated (HCD14; Biolegend; 1:20), CD44 FITC-conjugated (G44-26; BD Pharmingen; 1:10), and PDL1 were purchased commercially. Lung cancer cell lines and primary lung cancer cells were stained by CD14 staining in PBS at room temperature for 30 minutes. After 30 minutes, stained cells were washed to remove excess unbound antibodies and resuspended in sorting buffer (1 mM EDTA and 2% FBS in PBS). Flow sorting was done using a BD FACSAriaIII cell sorter (Becton Dickinson), and analysis was done on a FACSCalibur (BectonDickinson). To ensure single cell sorting, cell aggregates were eliminated by forward-scatter height versus forward-scatter width (FSC-H versus FSC-W) and side-scatter area versus side-scatter width (SSC-A versus SSC-W). Dead cells were eliminated by excluding propidium iodide (PI, dead cell stain, Molecular Probes) cells, which increased the efficiency of sorting robust, live cells for single-cell experiments.

Western Blot Analyses

Western blot analysis was performed according to standard procedures. The primary antibodies for p-JAK1 (Tyr1022/1023, 3331S), JAK1 (3344S), pSTAT1 (Tyr701, 9167S), STAT1 (9172S), pSTAT3 (Tyr705, 9131S), STAT3 (9139S), Nanog (D73G4; 1:1000) were purchased from Cell Signaling Technology, Inc., and the primary antibody for CD14 (EPR3653; 1:1000) was purchased from Cell marque. Monoclonal mouse anti-β-actin (Chemicon, Millipore; 1:5000) was used as a loading control. The membranes were washed three times with TBST, followed by incubation with horseradish peroxidase (HRP)-conjugated secondary antibody (1:5,000) in 2% skim milk/TBST. Bound antibody was detected using the Enhanced Chemiluminescence System (Santa Cruz, Calif.). Chemiluminescent signals were captured using the Fujifilm LAS 3000 system (Fujifilm, Tokyo, Japan). All experiments were performed at least three times in duplicate.

Results

Figure 3A:
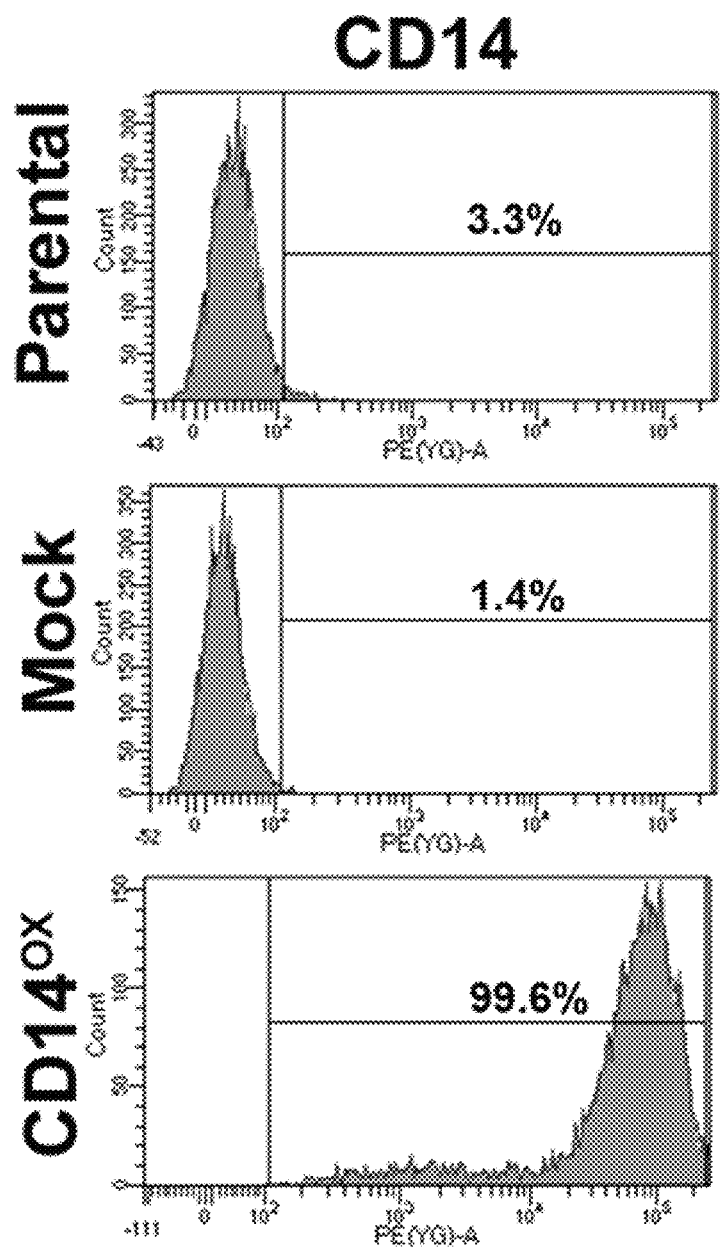
FIGS. 3A-3H show the effects of CD14 overexpression on cellular signaling. Flow cytometric analysis of CD14 in CLS1 cells overexpressing CD14 (FIG. 3A). Western blot analysis of JAK, STAT1, STAT5 and Nanog expression in CLS1 cells overexpressing CD14 (FIG. 3B). Metacore pathway analysis of genes up-regulated in CLS1 cells overexpressing CD14 compared to mock cells (FIG. 3C). Real-time RT Q-PCR analysis of stemness pathway molecules (CD14, CD44 and ALDH1A1), ABC transporters (ABCG1 and ABCG2), and an immune checkpoint molecule (PDL1) in CD14 overexpressing cells and mock cells (FIG. 3D). Data represent the mean±S.D. and tested for significance by Student's t-test *P<0.05. Data are representative of three independent biological experiments. Flow cytometric analysis of PDL1 in CD14 overexpressing CLS1 cells (FIG. 3E). Flow cytometric analysis of CD44 in CD14 overexpressing CLS1 cells (FIG. 3F). Flow cytometric analysis of doubly stained (CD14 and CD44) CLS1 cells overexpressing CD14 (FIG. 3G). Real-time (RT) Q-PCR analysis of PDL1 and CD44 expression levels in the CD14 overexpressed cells treated with anti-CD14 antibody (0.1 and 1 µg/ml) for 24 hours (FIG. 3H). Data represent the mean±S.E.M. Data was tested for significance by Student's t-test *P<0.05. Data are representative of three independent biological experiments.
Figure 3B:
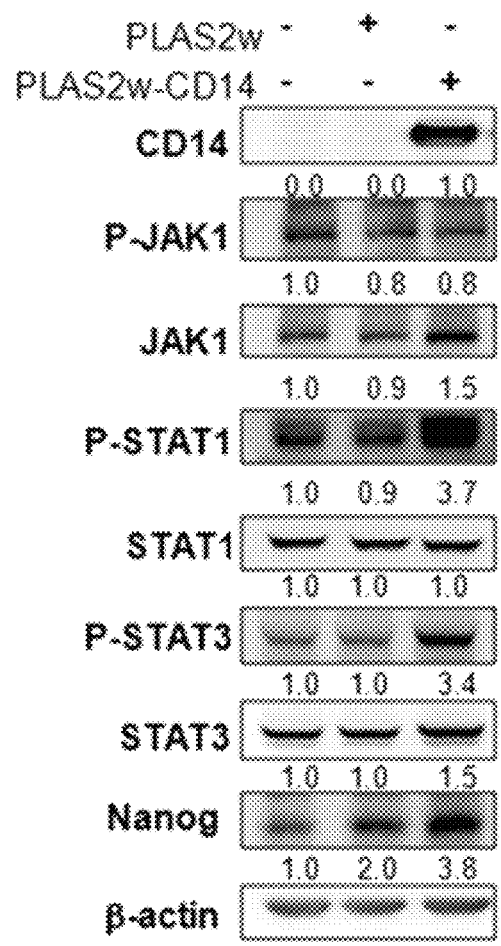
Figure 3C:
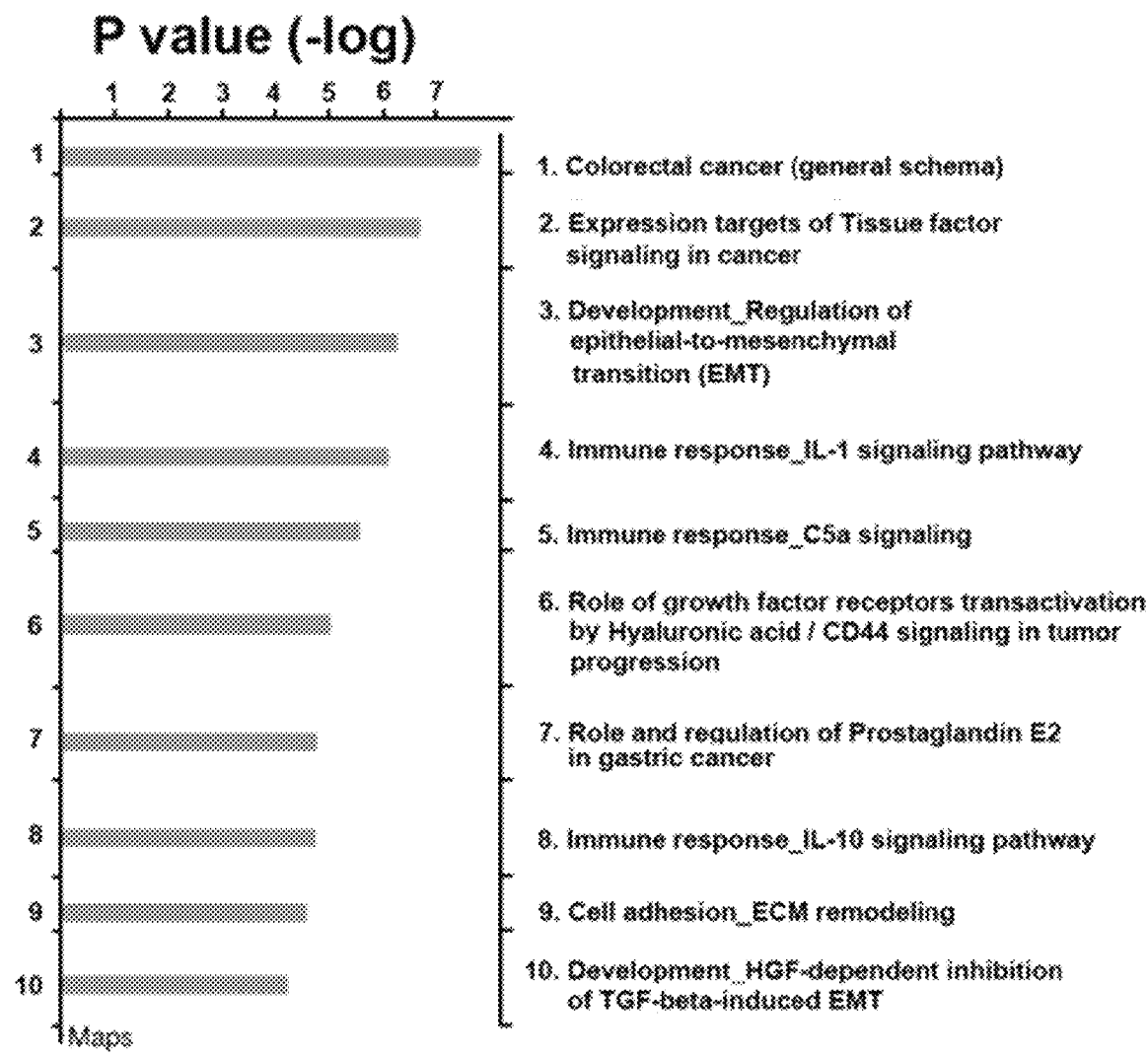
Figure 3D:
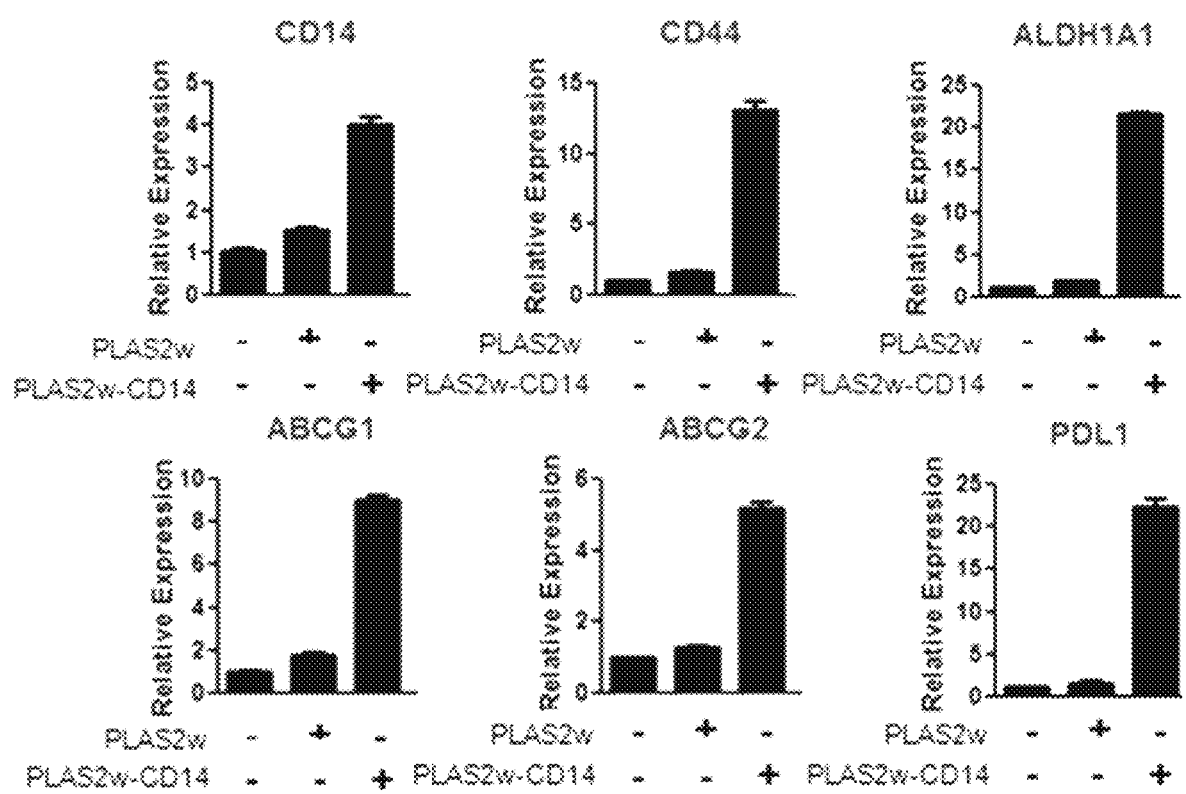
Figure 3E:
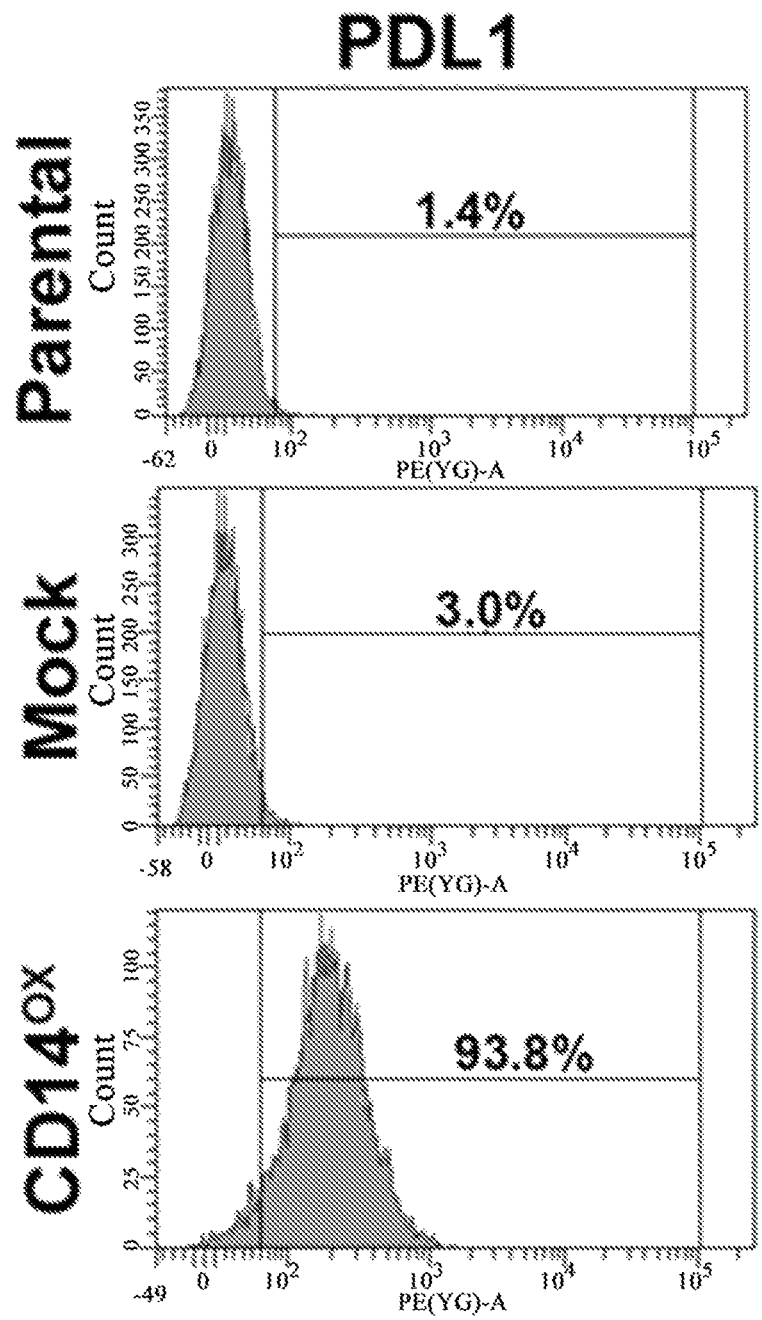
Figure 3F:
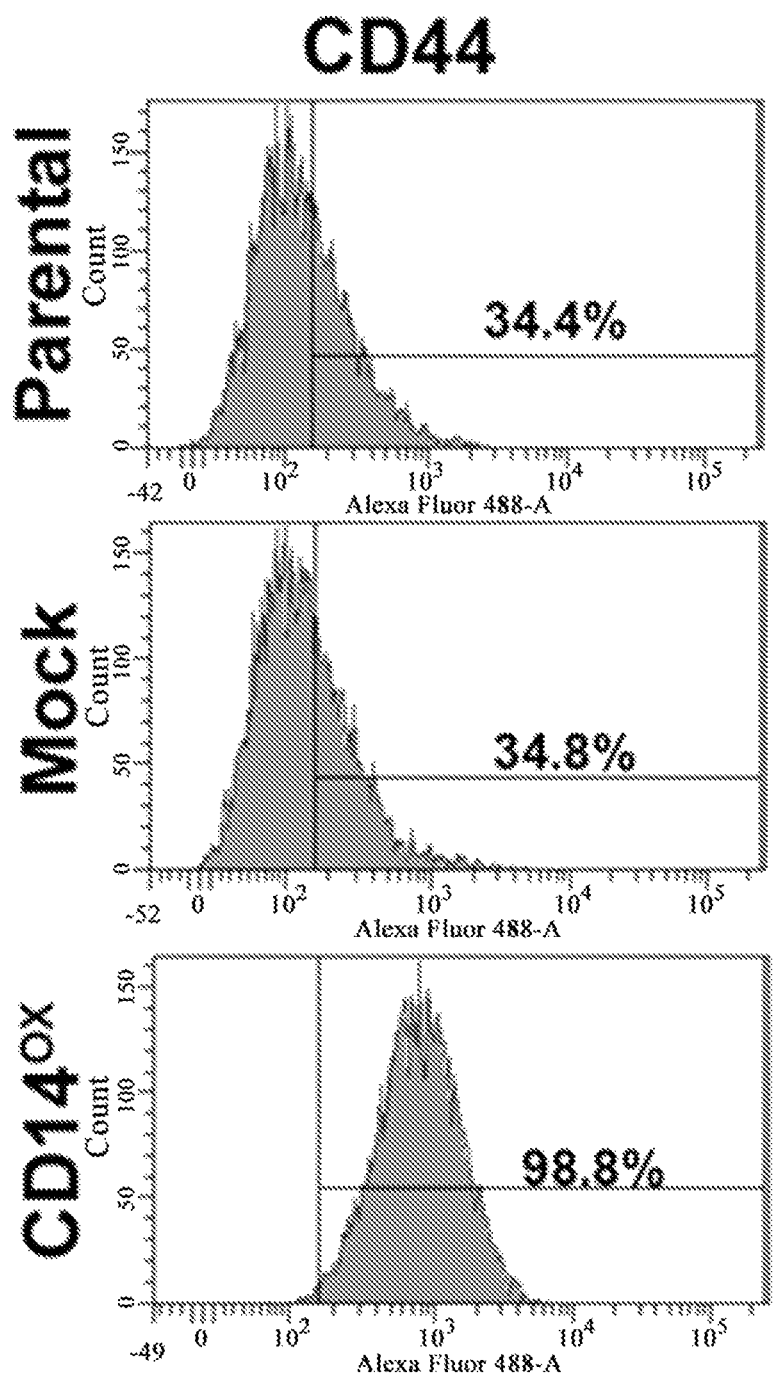
Figure 3G:
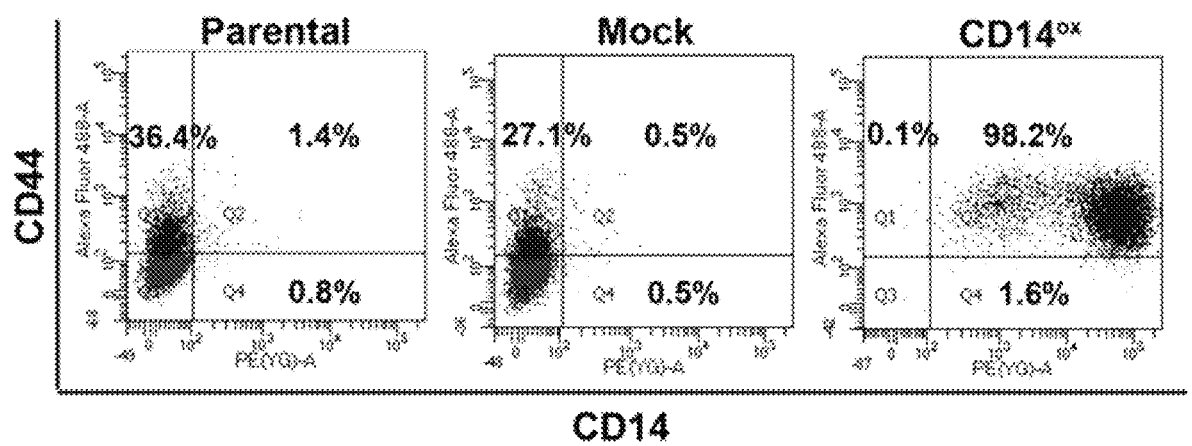
Figure 3H:
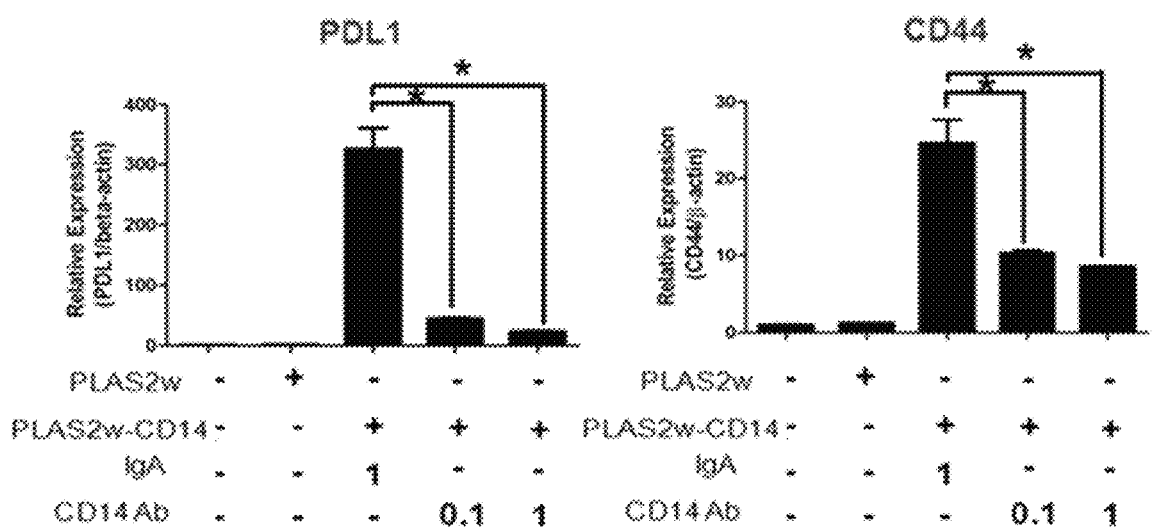

Several Pathways are Involved in Maintaining Cancer Stemness in CD14$^+$ Lung CSCs To understand how CD14 contributes to lung cancer stemness, CD14 was overexpressed in CLS1 cells (FIG. 3A). Western blotting showed that CD14 overexpression induced JAK1, STAT1, and STAT3 phosphorylation, and expression of Nanog (FIG. 3B). To uncover CD14-specific signaling pathways in lung CSCs, the transcriptional regulation network in the CD14 overexpression CLS1 cells was studied. According to the transcriptome and MetaCore software analysis, signaling pathways up-regulated in CD14 overexpression lung CSCs were related to colorectal cancer general schema (IL6 and IL8 signaling), epithelial-mesenchymal transition (EMT), CD44, HGF and TGF-β pathways, which regulate several stemness transcriptional factors such as Nanog, and immune response signaling such as ILL C5a and IL10 (FIG. 3C). Several of the key regulators identified, including CD44, ALDH1A1, ABC transporter and PDL1, were validated by Q-PCR (FIG. 3D). Increased expression of PDL1 (FIG. 3E) and CD44 (FIG. 3F) in CD14 overexpression lung cancer cells was confirmed by flow cytometry. Increased expression of CD44 was also detected in flow cytometric analysis of CD44 and CD14 doubly stained in CD14 overexpression CLS1 cells (FIG. 3G). Expression levels measured by RT Q-PCR showed that the increased expression of PDL1 and CD44 was inhibited in the CD14 overexpression cells treated with the anti-CD14 antibody (FIG. 3H).

The results obtained from this example indicate that CD14-mediated signaling pathway plays an important role in maintaining stemness of cancer stem cells. Thus, agents that block this signaling pathway would be expected to benefit cancer treatment.

Example 3: sCD14 Regulates Cancer Cell Stemness Through the JAK Signaling Pathway Materials and Methods Enzyme-Linked Immunosorbent Assay (ELISA)

For the quantitative determination of human soluble CD14 (sCD14) protein levels secreted to the media, sCD14 ELISA (Quantikine ELISA Human sCD14 Immunoassay, R&D Systems, Minneapolis, Minn., USA) were used according to the manufacturer's instructions. Conditioned medium of CAF cultures, CLS1/CAF co-cultures and CLS1 cultures were collected after 24 h in serum-free medium and 100 μL of the conditioned medium was used for sCD14 quantitative determination.

Human Receptor Tyrosine Kinase Phosphorylation Antibody Arrays

Human phosphorylation antibody arrays (G Series 1, Ray Biotech, Inc.) were used according to the manufacturer's instructions. Briefly, cell lysates from CLS1 cells treated with sCD14 (200 ng/ml) at different time points (0, 30, 60 min) were collected and incubated with the blocked glass array for 24 h at 4° C. with gentle shaking. After development, the fluorescence signals were scanned and quantification using the GenePix 4000B (Molecular Devices). The quantification of the fluorescence signal was normalized to that of the internal positive control.

Results sCD14 Regulates Cancer Cell Stemness Through the JAK Signaling Pathway

Figure 4A:
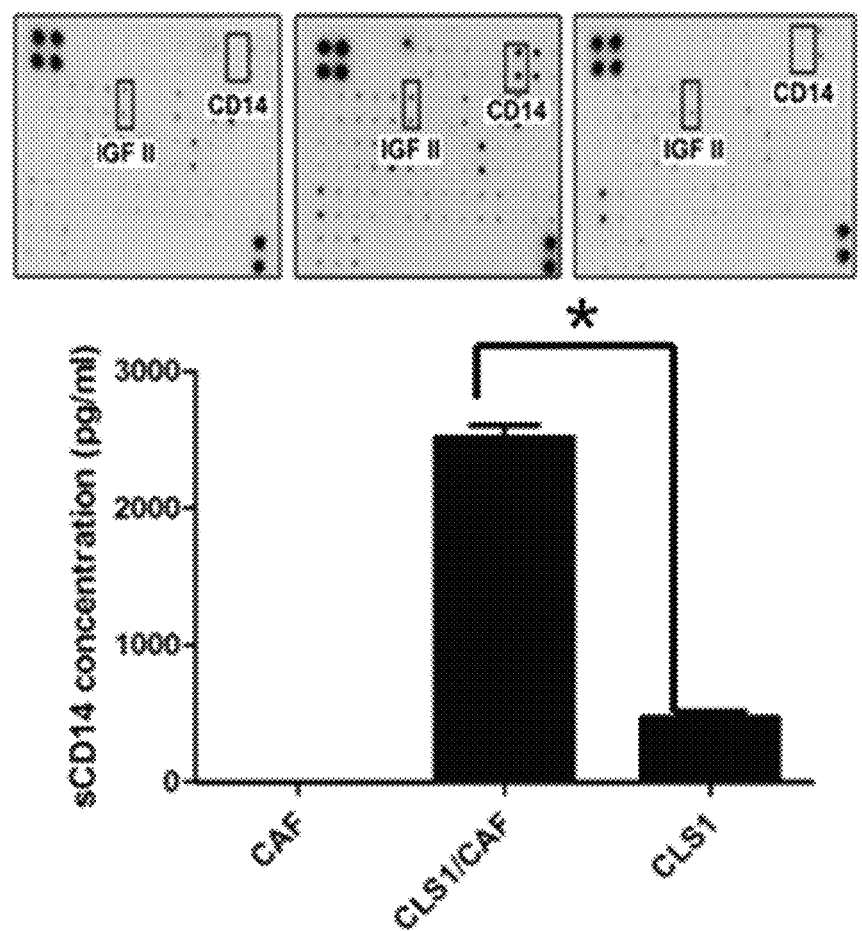
FIGS. 4A-4H show the regulatory effects of sCD14 on stemness properties in cancer cells. The concentration of secreted sCD14 in CAFs and CLS1 cells which co-cultured with CAFs or without CAFs were measured by ELISA (N=3) (FIG. 4A). Real-time RT Q-PCR analysis of stemness pathway molecules (Nanog, Oct3/4 and Sox2) in CLS1 cells treated with or without sCD14 (200 ng/ml) for 72 hours (FIG. 4B). Data represent the mean±S.E.M and tested for significance by Student's t-test *P<0.05. Data are representative of three independent biological experiments each. The sphere-forming ability (lower panel) and morphology (upper panel) of primary lung cancer cell (CL141 and CL152 cells) treated with sCD14 in MCDB201 medium plus EGF (20 ng/ml) and bFGF (20 ng/ml) for 21 days (FIG. 4C). Receptor tyrosine kinase phosphorylation antibody arrays were used to identify potential signaling of the CLS1 cells treated with or without sCD14 (200 ng/ml) for 30 mins and 1 h. The arrays were scanned and quantified, and the levels were normalized to those of the positive controls (FIG. 4D). Western blot analysis of JAK1 and Nanog expression in CLS1 cells treated with sCD14 (200 ng/ml) treated with IGF-II (100 ng/ml) at the indicated time points (0, 10 and 30 min and 1, 2, 6 and 24 h) (FIG. 4E). Protein levels of LIFR and Nanog-targeting shRNA LIFR (shLIFR #659 and shLIFR #362) or scrambled siRNA (shLuc) cells were examined through immunoblotting. β-Actin was used as an internal control (FIG. 4F). Protein levels of JAK and Nanog-targeting shRNA LIFR (shLIFR #659 and shLIFR #362) or scrambled siRNA (shLuc) cells treated with sCD14 (200 ng/ml) at the indicated time points (0, 10 and 30 min and 1, 2, 6 and 24 h) were examined through immunoblotting. β-Actin was used as an internal control (FIG. 4G). Sphere-forming ability and morphology of CLS1 cells treated with sCD14 (200 ng/ml) and analysis of the specific knockdown of LIFR after culturing in MCDB201 medium with EGF (20 ng/ml) and bFGF (20 ng/ml) for 21 days (FIG. 4H). Scale bar, 100 µm.
Figure 4B:
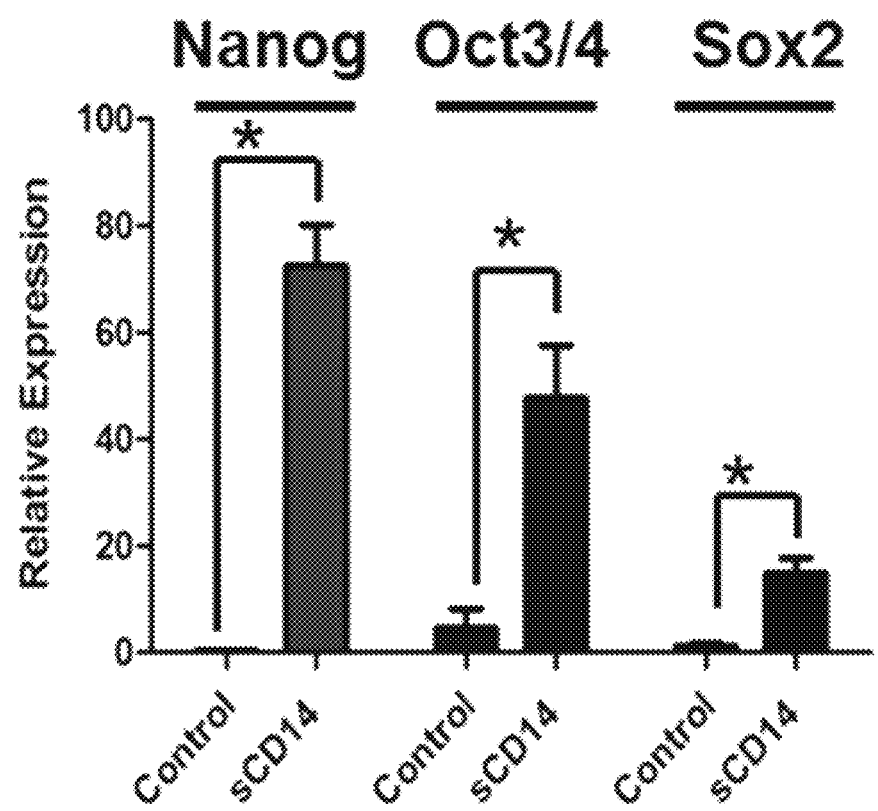
Figure 4C:
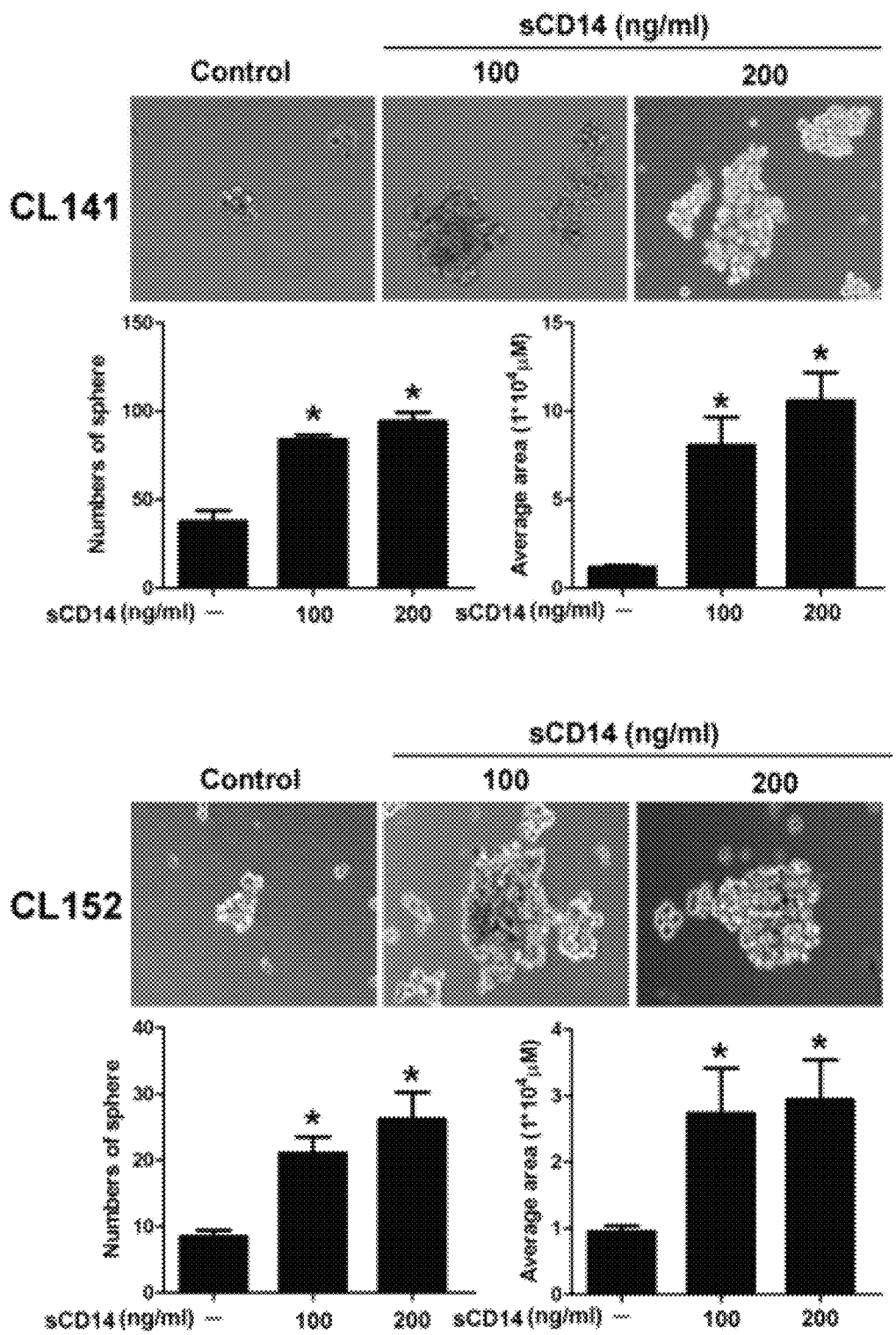

To further understand how CD14 contributes to lung cancer stemness, the role of sCD14 in maintaining cancer cell stemness was evaluated. Using an ELISA assay, it was shown that sCD14 was highly secreted into the media of CLS1/CAFs co-cultures, but not the media of cultured CAFs and CLS1 cells (FIG. 4A). CLS1 cells treated with sCD14 (200 ng/ml) showed increased expression of the cancer stemness pathway molecules (Nanog, Oct3/4, and Sox2) compared to CLS1 cells without sCD14 treatment (FIG. 4B). Sphere-forming ability and stem cell morphology were induced in primary lung cancer cells (CL141 and CL152) treated with sCD14 (FIG. 4C).

Figure 4D:
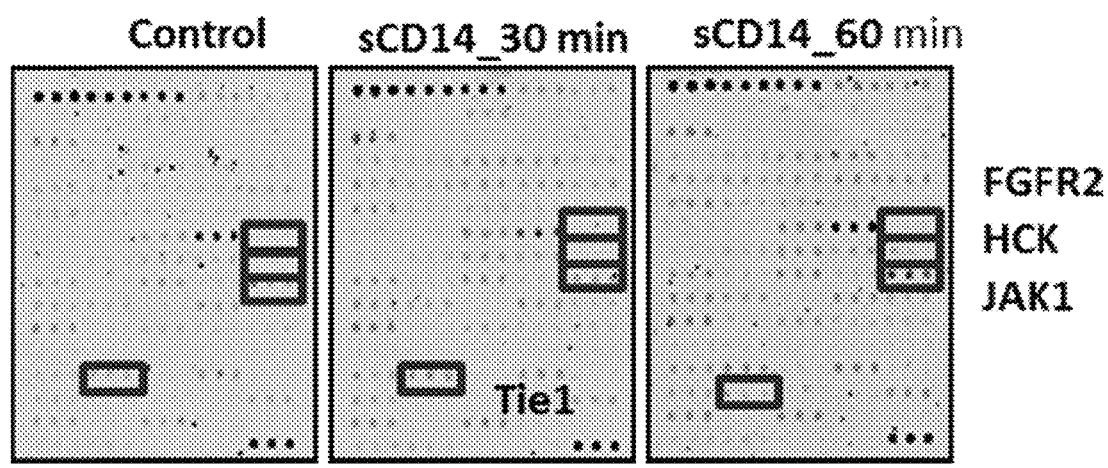
Figure 4E:
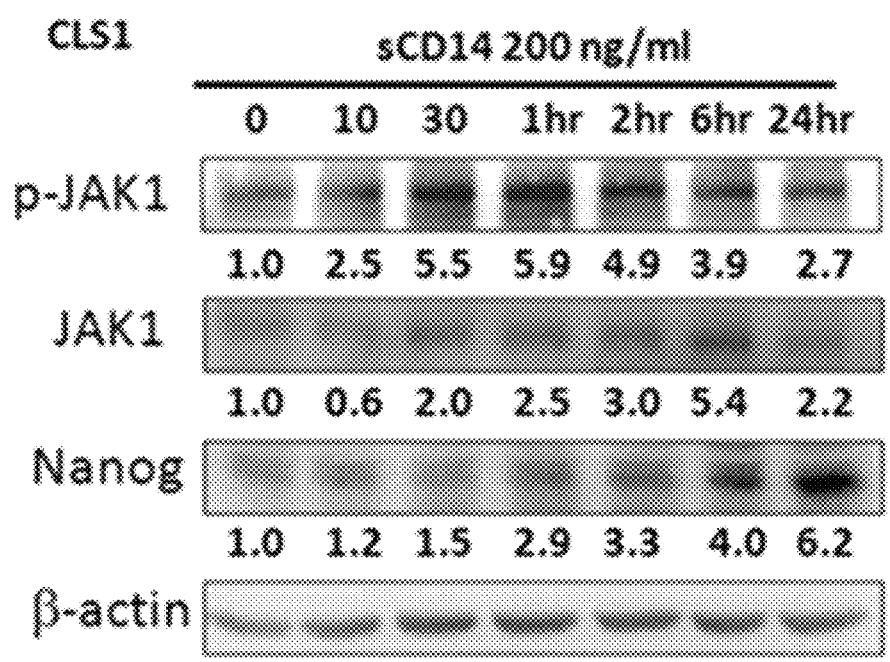

To understand how sCD14 regulates cancer stemness, proteins in which phosphorylation was induced by sCD14 were identified using the Human RTK Phosphorylation Antibody Array (Ray Biotech, Inc., Norcross Ga.). These experiments demonstrated that JAK1 phosphorylation was induced in a time dependent manner by sCD14 (FIG. 4D). Western blotting further confirmed that sCD14 induced JAK1 phosphorylation and Nanog expression in a time dependent manner in primary lung cancer cells (CLS1; FIG. 4E).

Figure 4F:
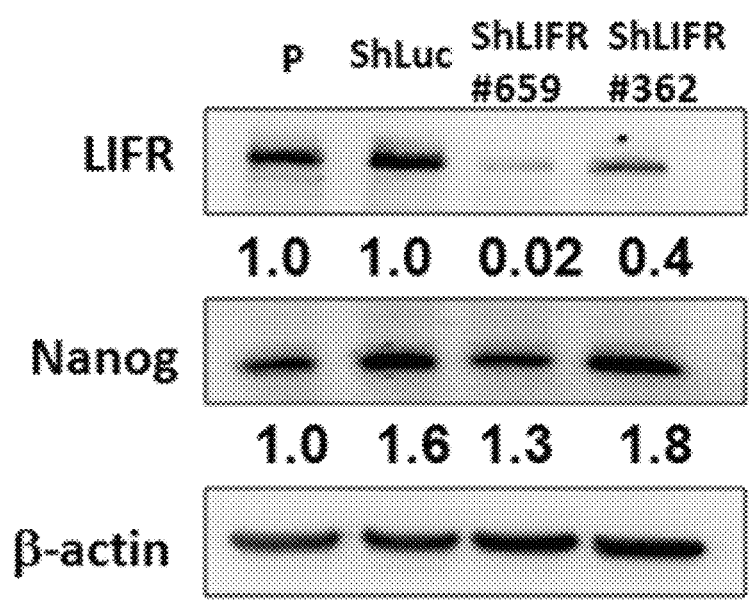
Figure 4G:
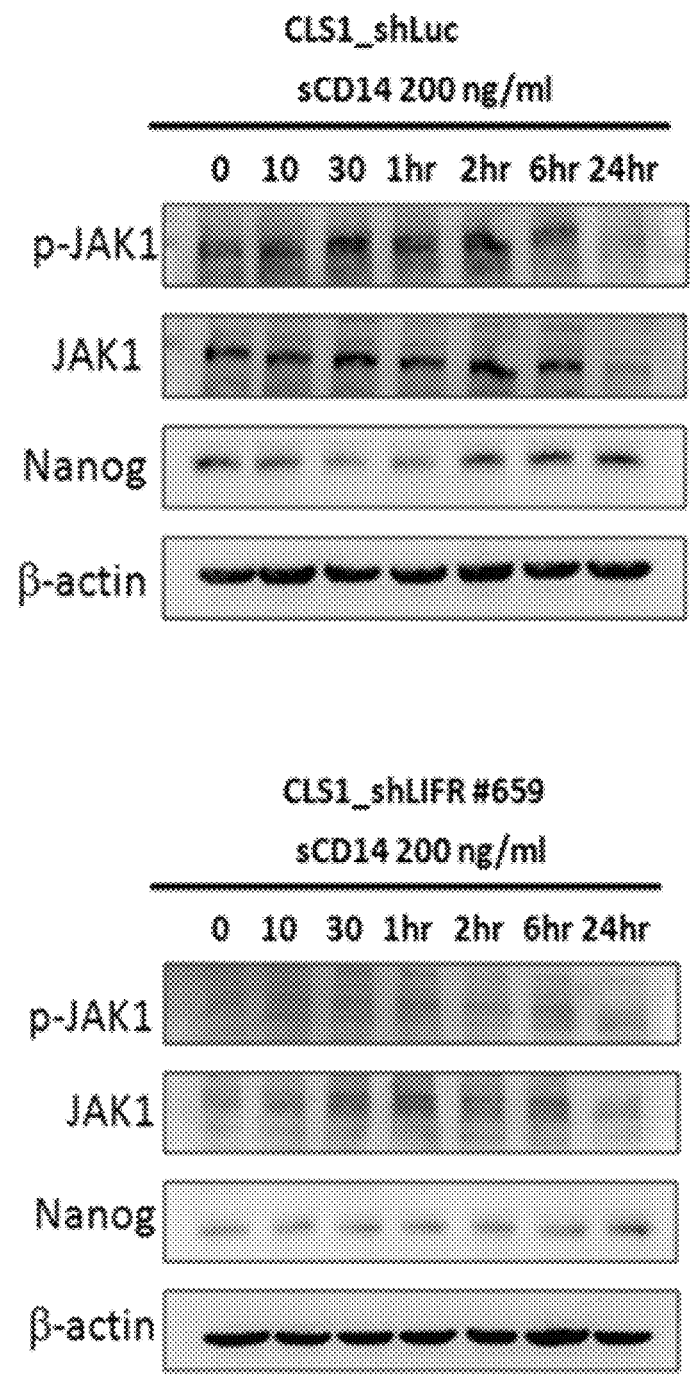
Figure 4H:
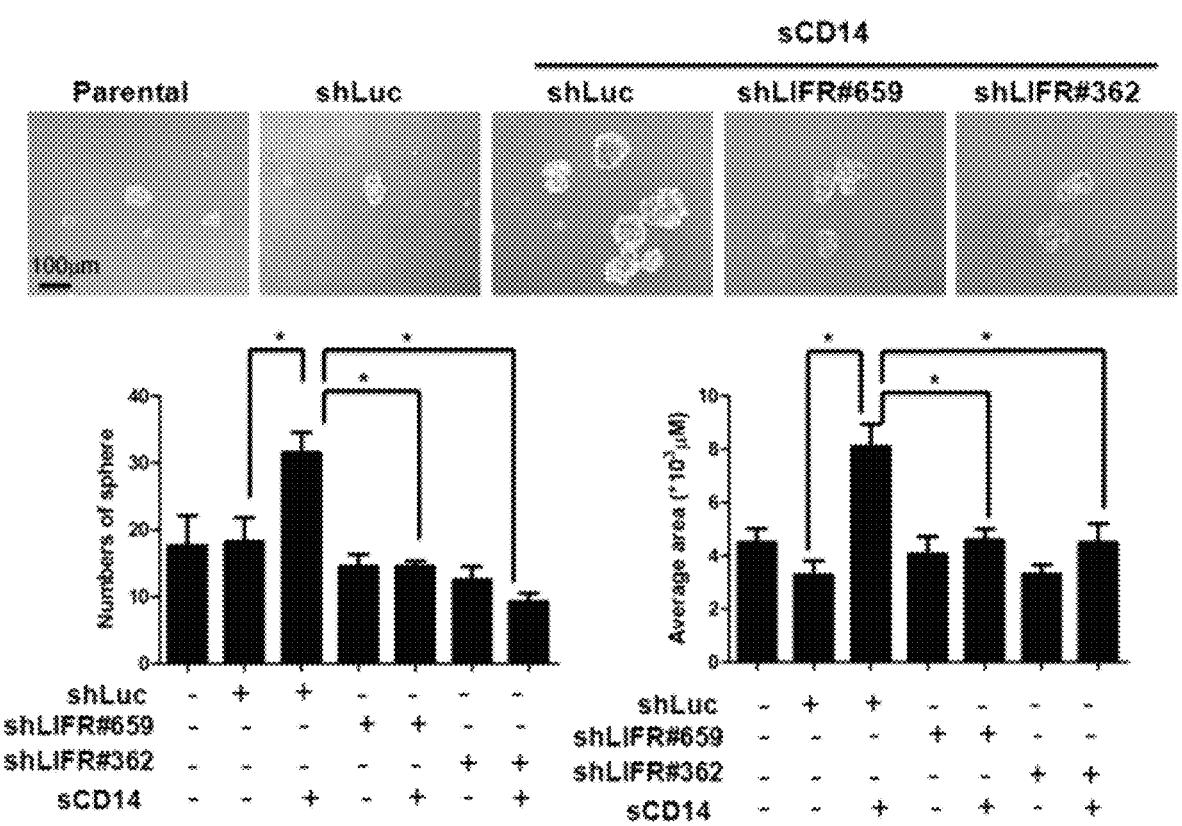

Cell differentiation is affected by interaction of leukemia inhibitory factor (LIF) with the leukemia inhibitory factor receptor (LIFR). When LIF levels in the cells are low, cells differentiate. sCD14-regulated cancer stemness was inhibited by knockdown of leukemia inhibitory factor receptor (LIFR). Knockdown of LIFR was demonstrated using two different shRNA against LIFR (FIG. 4F). LIFR knockdown inhibited sCD14-induced JAK1 phosphorylation and Nanog expression (FIG. 4G), and sphere-formation (FIG. 4H).

The results obtained from this example indicate that sCD14 plays an important role in maintaining sternness of cancer stem cells, and that sCD14 induced sternness through LIFR/JAK1 signaling. Thus, agents that block this signaling pathway would be expected to benefit cancer treatment.

Example 4: sCD14 Increased Expression of the Immunosuppressive Ligand PD-L1

Figure 5A:
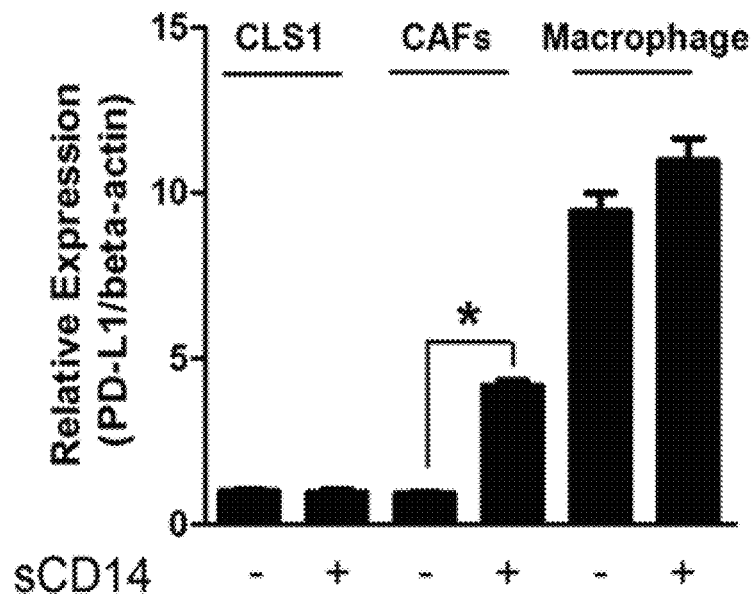
FIGS. 5A-5C show the regulatory effects of sCD14 on immunoinhibitory molecules in tumor microenvironment. Real-time RT Q-PCR analysis of PDL1 in cancer cell, CAFs and THP1 derived macrophage treated with sCD14 (200 ng/ml) for 24 hours (FIG. 5A). Real-time RT Q-PCR analysis of PDL1 in THP1 derived macrophage treated with serial concentration of sCD14 (0, 20, 200 and 1000 ng/ml) and anti-CD14 antibody (1 µg/ml) for 24 hours (FIG. 5B). Flow cytometric analysis of PDL1 in THP1 derived macrophage treated with serial concentration of sCD14 (0, 20, 200 and 1000 ng/ml) or sCD14 in combination with anti-CD14 antibody (0.2 and 1 µg/ml) (FIG. 5C).
Figure 5B:
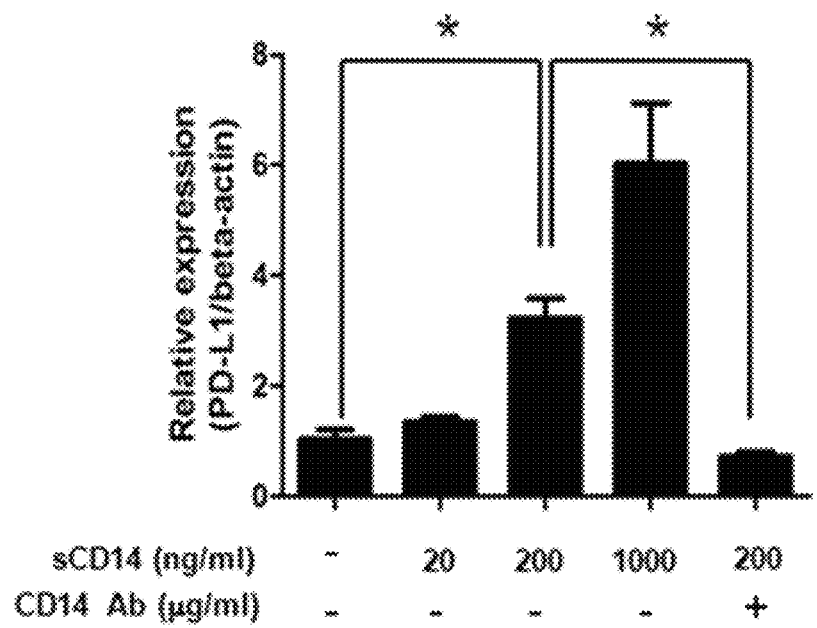
Figure 5C:
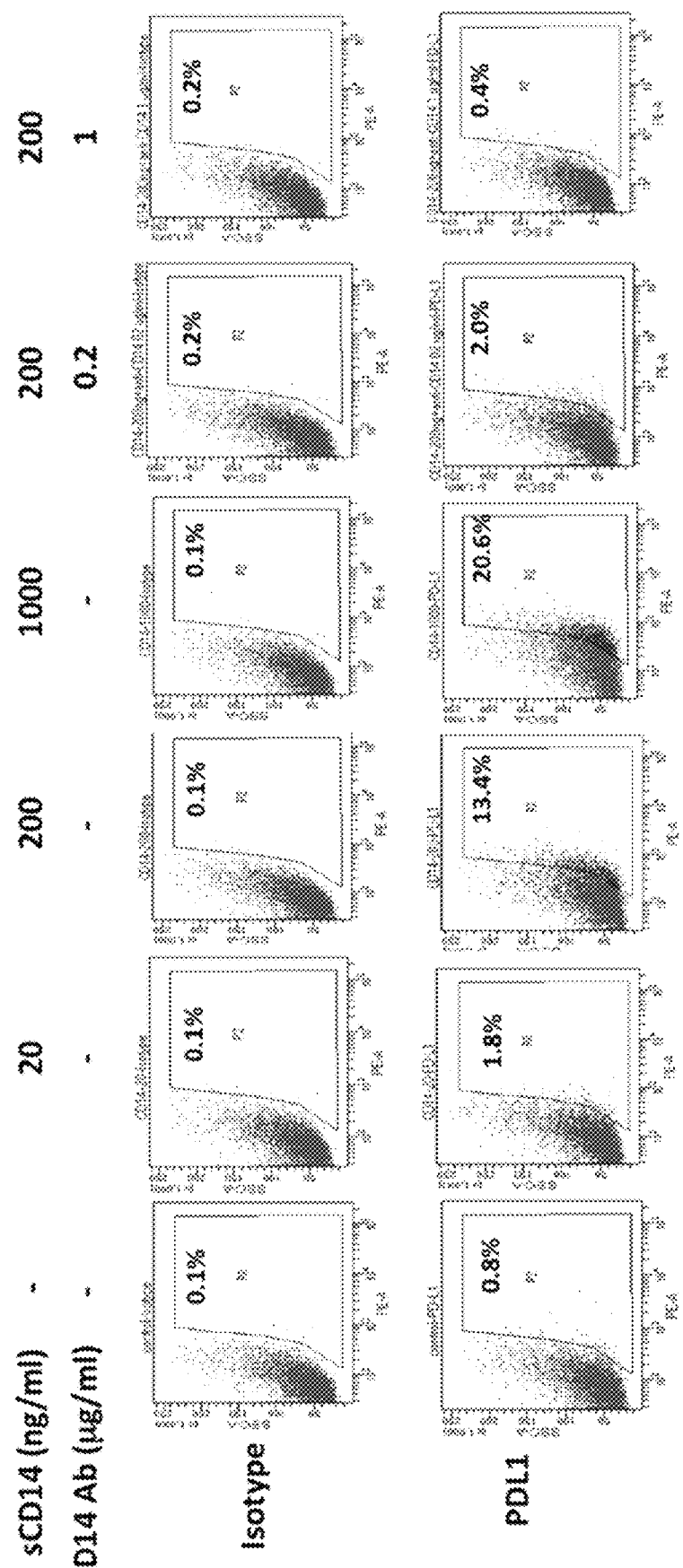

To investigate whether sCD14 increases the immunosuppressive abilities in the tumor microenvironment, the expression level of the immunosuppressive ligand PD-L1 was analyzed in cancer cells, CAFs, and macrophages treated with sCD14. Macrophages treated with CD14 demonstrated increased PD-L1 expression compared to cancer cells and CAFs treated with sCD14 (FIG. 5A). sCD14-induced expression of PD-L1 in macrophages in a dose dependent manner (FIG. 5B-5C). sCD14-induced PD-L1 expression was inhibited in macrophages treated with anti-CD14 antibody (FIG. 5B-5C).

The results obtained from this example indicate that sCD14 increases expression of the immunosuppressive ligand PD-L1 in macrophages, thereby promoting the immunosuppressive abilities of macrophages in the tumor microenvironment.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features. From the above description, one skilled in the art can easily ascertain the essential characteristics of the present disclosure, and without departing from the spirit and scope thereof, can make various changes and modifications of the present disclosure to adapt it to various usages and conditions. Thus, other embodiments are also within the claims.

EQUIVALENTS AND SCOPE

Those skilled in the art will recognize, or be able to ascertain using no more than routine experimentation, many equivalents to the specific embodiments of the present disclosure described herein. The scope of the present disclosure is not intended to be limited to the above description, but rather is as set forth in the appended claims.

In the claims articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The present disclosure includes embodiments in which exactly one member of the group is present in, employed in, or otherwise relevant to a given product or process. The present disclosure includes embodiments in which more than one, or all of the group members are present in, employed in, or otherwise relevant to a given product or process.

Furthermore, the present disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the present disclosure, or aspects of the present disclosure, is/are referred to as comprising particular elements and/or features, certain embodiments of the present disclosure or aspects of the present disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the present disclosure, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims. Because such embodiments are deemed to be known to one of ordinary skill in the art, they may be excluded even if the exclusion is not set forth explicitly herein. Any particular embodiment of the present disclosure can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A method for treating cancer, comprising:
administering to a subject in need thereof an effective amount of a CD14 antagonist, wherein the subject is a human subject having cancer;
wherein the CD14 antagonist is effective in reducing stemness of cancer stem cells (CSCs) in the human subject having cancer;
wherein the human subject having cancer has an elevated level of CD14, an elevated level of programmed death ligand-1 (PDL1), and an elevated level of CD44, as compared to a control human subject not having cancer;
wherein the cancer is lung cancer;
wherein the CD14 antagonist is an anti-CD14 antibody;
wherein the anti-CD14 antibody is an antigen-binding fragment thereof; and
wherein the anti-CD14 antibody comprises six complementarity determining regions (CDRs) of anti-hCD14-IgA2 antibody, clone D3B8.

2. The method of claim 1, wherein the anti-CD14 antibody is a human antibody or a humanized antibody.

3. The method of claim 1, wherein the anti-CD14 antibody is conjugated to a toxin.

4. The method of claim 1, wherein the lung cancer is non-small-cell-lung-cancer (NSCLC).

5. The method of claim 1, wherein the amount of anti-CD14 antibody is effective in reducing tumor formation or tumor growth.

6. The method of claim 1, wherein the anti-CD14 antibody is formulated in a pharmaceutical composition, which further comprises a pharmaceutically acceptable carrier.

7. The method of claim 1, further comprising administering to the subject another anti-cancer therapeutic agent.

8. The method of claim 1, wherein the subject is on or has been subject to another anti-cancer therapy.

9. The method of claim 1, wherein the anti-CD14 antibody is administered systemically.

10. The method of claim 9, wherein the anti-CD14 antibody is administered via a parenteral route.

11. The method of claim 1, wherein the amount of the anti-CD14 antibody is effective in inhibiting cancer stem cell-induced immunosuppression.

12. The method of claim 11, wherein the cancer stem cell-induced immunosuppression is an increased expression of PDL1 in immune cells, cancer cells, or a combination thereof.

* * * * *

SEQUENCE LISTING

```
<160> NUMBER OF SEQ ID NOS: 14

<210> SEQ ID NO 1
<211> LENGTH: 23
<212> TYPE: DNA
<213> ORGANISM: Artificial sequence
<220> FEATURE:
<223> OTHER INFORMATION: Synthetic primer

<400> SEQUENCE: 1
cacagaggag ggaactgaat gac                                         23

<210> SEQ ID NO 2
<211> LENGTH: 20
<212> TYPE: DNA
<213> ORGANISM: Artificial sequence
<220> FEATURE:
<223> OTHER INFORMATION: Synthetic primer

<400> SEQUENCE: 2
aactcttcgg ctgcctctga                                             20

<210> SEQ ID NO 3
<211> LENGTH: 24
<212> TYPE: DNA
<213> ORGANISM: Artificial sequence
<220> FEATURE:
<223> OTHER INFORMATION: Synthetic primer

<400> SEQUENCE: 3
tggacactca catgggagtc aaga                                        24

<210> SEQ ID NO 4
<211> LENGTH: 20
<212> TYPE: DNA
<213> ORGANISM: Artificial sequence
<220> FEATURE:
<223> OTHER INFORMATION: Synthetic primer

<400> SEQUENCE: 4
cgactgttga ctgcaatgca                                             20

<210> SEQ ID NO 5
<211> LENGTH: 23
<212> TYPE: DNA
<213> ORGANISM: Artificial sequence
<220> FEATURE:
<223> OTHER INFORMATION: Synthetic primer

<400> SEQUENCE: 5
tccagcccac agtgttctct aat                                         23

<210> SEQ ID NO 6
<211> LENGTH: 24
<212> TYPE: DNA
```

<213> ORGANISM: Artificial sequence
<220> FEATURE:
<223> OTHER INFORMATION: Synthetic primer

<400> SEQUENCE: 6
actggtccaa aaatctcctc tttg                                          24

<210> SEQ ID NO 7
<211> LENGTH: 22
<212> TYPE: DNA
<213> ORGANISM: Artificial sequence
<220> FEATURE:
<223> OTHER INFORMATION: Synthetic primer

<400> SEQUENCE: 7
ccagctttac gtcctgagtc aa                                            22

<210> SEQ ID NO 8
<211> LENGTH: 22
<212> TYPE: DNA
<213> ORGANISM: Artificial sequence
<220> FEATURE:
<223> OTHER INFORMATION: Synthetic primer

<400> SEQUENCE: 8
gacccaaatc cctcaaatat gg                                            22

<210> SEQ ID NO 9
<211> LENGTH: 26
<212> TYPE: DNA
<213> ORGANISM: Artificial sequence
<220> FEATURE:
<223> OTHER INFORMATION: Synthetic primer

<400> SEQUENCE: 9
gctcagatca ttgtcacagt cgtact                                        26

<210> SEQ ID NO 10
<211> LENGTH: 23
<212> TYPE: DNA
<213> ORGANISM: Artificial sequence
<220> FEATURE:
<223> OTHER INFORMATION: Synthetic primer

<400> SEQUENCE: 10
gttggtcgtc aggaagaaga gaa                                           23

<210> SEQ ID NO 11
<211> LENGTH: 20
<212> TYPE: DNA
<213> ORGANISM: Artificial sequence
<220> FEATURE:
<223> OTHER INFORMATION: Synthetic primer

<400> SEQUENCE: 11
cctctggcac atcctccaaa                                               20

<210> SEQ ID NO 12
<211> LENGTH: 24
<212> TYPE: DNA
<213> ORGANISM: Artificial sequence
<220> FEATURE:
<223> OTHER INFORMATION: Synthetic primer

<400> SEQUENCE: 12
tcacatccat cattctccct tttc                                          24

```
<210> SEQ ID NO 13
<211> LENGTH: 20
<212> TYPE: DNA
<213> ORGANISM: Artificial sequence
<220> FEATURE:
<223> OTHER INFORMATION: Synthetic primer

<400> SEQUENCE: 13
ctggaacggt gaaggtgaca                                         20

<210> SEQ ID NO 14
<211> LENGTH: 20
<212> TYPE: DNA
<213> ORGANISM: Artificial sequence
<220> FEATURE:
<223> OTHER INFORMATION: Synthetic primer

<400> SEQUENCE: 14
cggccacatt gtgaactttg                                         20
```